United States Patent
Gachotte et al.

(10) Patent No.: US 9,617,555 B2
(45) Date of Patent: *Apr. 11, 2017

(54) GENERATION OF TRANSGENIC CANOLA WITH LOW OR NO SATURATED FATTY ACIDS

(71) Applicant: Dow AgroSciences LLC, Indianapolis, IN (US)

(72) Inventors: Daniel J. Gachotte, Indianapolis, IN (US); Ann Owens Merlo, Carmel, IN (US); Mark A. Thompson, Zionsville, IN (US); Terence A. Walsh, Carmel, IN (US); Beth Rubin Wilson, Indianapolis, IN (US); Mary Welter, Indianapolis, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/578,008

(22) Filed: Dec. 19, 2014

(65) Prior Publication Data

US 2015/0191738 A1    Jul. 9, 2015

Related U.S. Application Data

(63) Continuation-in-part of application No. 13/168,742, filed on Jun. 24, 2011, which is a continuation-in-part of application No. 11/576,750, filed as application No. PCT/US2005/035052 on Oct. 7, 2005.

(60) Provisional application No. 60/617,532, filed on Oct. 8, 2004.

(51) Int. Cl.
*C12N 15/82* (2006.01)
*C12N 5/14* (2006.01)
*C12N 9/02* (2006.01)

(52) U.S. Cl.
CPC ....... *C12N 15/8247* (2013.01); *C12N 9/0083* (2013.01); *C12N 5/14* (2013.01); *C12Y 114/19001* (2013.01)

(58) Field of Classification Search
None
See application file for complete search history.

(56) References Cited

U.S. PATENT DOCUMENTS

| | | | |
|---|---|---|---|
| 5,777,201 A | 7/1998 | Poutre et al. | |
| 6,495,738 B1 * | 12/2002 | Folkerts | C12N 9/0083 435/419 |
| 6,825,335 B1 * | 11/2004 | Martin | C12N 15/8247 435/183 |
| 2006/0080750 A1 | 4/2006 | Fillatti et al. | |
| 2008/0092254 A1 | 4/2008 | Shah et al. | |
| 2011/0302672 A1 | 12/2011 | Merlo et al. | |

OTHER PUBLICATIONS

Gelvin 2003 (Microbiology and Molecular Biology Reviews March: p. 16-37).*
International Search Report and Written Opinion for PCT/US2014/071705, dated Jul. 29, 2015.

* cited by examiner

*Primary Examiner* — Matthew Keogh
(74) *Attorney, Agent, or Firm* — Marcia I. Rosenfeld; Magleby Cataxinos & Greenwood

(57) ABSTRACT

Compositions and methods include genetically encoding and expressing a novel delta-9 desaturase in plant cells. In some embodiments, methods of expressing nucleic acids in a plant cell to take advantage of the delta-9 desaturase enzyme's activity, such that the percent composition of saturated fatty acids in plant seeds is decreased and there is a concomitant increase in $\Delta 9$ fatty acids. In other embodiments, amino acid sequences have delta-9 desaturase activity. Methods can involve expression of delta-9 desaturase in plant cells, plant materials, and whole plants for the purpose of increasing the amount of mono unsaturated fatty acids in whole plants, plant seeds, and plant materials, for example, seeds.

6 Claims, 5 Drawing Sheets

SEQUENCE LISTING

<160> NUMBER OF SEQ ID NOS: 33

<210> SEQ ID NO 1
<211> LENGTH: 455
<212> TYPE: PRT
<213> ORGANISM: Aspergillus nidulans

<400> SEQUENCE: 1

Met Ser Ala Pro Thr Ala Asp Ile Arg Ala Arg Ala Pro Glu Ala Lys
1               5                   10                  15

Lys Val His Ile Ala Asp Thr Ala Ile Asn Arg His Asn Trp Tyr Lys
            20                  25                  30

```
His Val Asn Trp Leu Asn Val Phe Leu Ile Ile Gly Ile Pro Leu Tyr
         35                  40                  45

Gly Cys Ile Gln Ala Phe Trp Val Pro Leu Gln Leu Lys Thr Ala Ile
 50                  55                  60

Trp Ala Val Ile Tyr Tyr Phe Phe Thr Gly Leu Gly Ile Thr Ala Gly
 65                  70                  75                  80

Tyr His Arg Leu Trp Ala His Cys Ser Tyr Ser Ala Thr Leu Pro Leu
                 85                  90                  95

Arg Ile Trp Leu Ala Ala Val Gly Gly Gly Ala Val Glu Gly Ser Ile
                100                 105                 110

Arg Trp Trp Ala Arg Asp His Arg Ala His His Arg Tyr Thr Asp Thr
                115                 120                 125

Asp Lys Asp Pro Tyr Ser Val Arg Lys Gly Leu Leu Tyr Ser His Leu
130                 135                 140

Gly Trp Met Val Met Lys Gln Asn Pro Lys Arg Ile Gly Arg Thr Asp
145                 150                 155                 160

Ile Ser Asp Leu Asn Glu Asp Pro Val Val Trp Gln His Arg Asn
                165                 170                 175

Tyr Leu Lys Val Val Phe Thr Met Gly Leu Ala Val Pro Met Leu Val
                180                 185                 190

Ala Gly Leu Gly Trp Gly Asp Trp Leu Gly Gly Phe Val Tyr Ala Gly
                195                 200                 205

Ile Leu Arg Ile Phe Phe Val Gln Gln Ala Thr Phe Cys Val Asn Ser
                210                 215                 220

Leu Ala His Trp Leu Gly Asp Gln Pro Phe Asp Asp Arg Asn Ser Pro
225                 230                 235                 240

Arg Asp His Val Ile Thr Ala Leu Val Thr Leu Gly Glu Gly Tyr His
                245                 250                 255

Asn Phe His His Glu Phe Pro Ser Asp Tyr Arg Asn Ala Ile Glu Trp
                260                 265                 270

His Gln Tyr Asp Pro Thr Lys Trp Ser Ile Trp Ala Trp Lys Gln Leu
                275                 280                 285

Gly Leu Ala Tyr Asp Leu Lys Lys Phe Arg Ala Asn Glu Ile Glu Lys
                290                 295                 300

Gly Arg Val Gln Gln Leu Gln Lys Lys Leu Asp Arg Lys Arg Ala Thr
305                 310                 315                 320

Leu Asp Trp Gly Thr Pro Leu Asp Gln Leu Pro Val Met Glu Trp Asp
                325                 330                 335

Asp Tyr Val Glu Gln Ala Lys Asn Gly Arg Gly Leu Val Ala Ile Ala
                340                 345                 350

Gly Val Val His Asp Val Thr Asp Phe Ile Lys Asp His Pro Gly Gly
                355                 360                 365

Lys Ala Met Ile Ser Ser Gly Ile Gly Lys Asp Ala Thr Ala Met Phe
370                 375                 380

Asn Gly Gly Val Tyr Tyr His Ser Asn Ala Ala His Asn Leu Leu Ser
385                 390                 395                 400

Thr Met Arg Val Gly Val Ile Arg Gly Gly Cys Glu Val Glu Ile Trp
                405                 410                 415

Lys Arg Ala Gln Lys Glu Asn Val Glu Tyr Val Arg Asp Gly Ser Gly
                420                 425                 430
```

Gln Arg Val Ile Arg Ala Gly Glu Gln Pro Thr Lys Ile Pro Glu Pro
        435                 440                 445

Ile Pro Thr Ala Asp Ala Ala
        450                 455

<210> SEQ ID NO 2
<211> LENGTH: 1368
<212> TYPE: DNA
<213> ORGANISM: Artificial Sequence
<220> FEATURE:
<223> OTHER INFORMATION: Synthesized nucleodtide encoding Aspergillus
      nidulas Delta 9 desaturase v3

<400> SEQUENCE: 2

```
atgtctgctc caaccgctga catcagggct agggctccag aggctaagaa ggttcacatc      60
gctgataccg ctatcaacag gcacaattgg tacaagcacg tgaactggct caacgtcttc     120
ctcatcatcg aatcccact ctacggatgc atccaagctt tctggttcc acttcaactc       180 aagaccgcta tctgggctgt gatctactac ttcttcaccg acttggaat caccgctgga      240 taccacaggc tttgggctca ctgctcatac tctgctactc ttccacttag gatctggctt     300
gctgctgttg gaggaggagc tgttgaggga tctatcagat ggtgggctag ggatcacagg     360
gctcatcata ggtacaccga taccgacaag gacccatact ctgttaggaa gggacttctc     420
tactctcacc ttggatggat ggtgatgaag cagaacccaa agaggatcgg aaggaccgac     480
atctctgatc tcaacgagga cccagttgtt gtttggcaac acaggaacta cctcaaggtt     540
gtgttcacca tgggacttgc tgttccaatg cttgttgctg acttggatg gggagattgg      600 cttggaggat tcgtgtacgc tggaatcctt aggatcttct tcgttcaaca agctaccttc     660
tgcgtgaact ctcttgctca ctggcttgga gatcaaccat tcgatgatag gaactctcct     720
agggatcacg tgatcaccgc tcttgttacc cttggagagg ataccacaa cttccaccac      780 gagttcccat ctgactacag gaacgctatc gagtggcacc agtacgatcc taccaagtgg     840
tctatctggg cttggaagca acttggattg gcttacgatc tcaagaagtt cagggctaac     900
gagatcgaga agggaagggt tcaacaactt cagaagaagc ttgataggaa gagggctact    960
cttgattggg gaaccccact tgatcaactt ccagtgatgg aatgggatga ctacgttgag    1020
caagctaaga acggaagggg acttgttgct atcgctggag ttgttcacga tgttaccgac    1080
ttcatcaagg atcacccagg aggaaaggct atgatctctt ctggaatcgg aaaggatgct    1140
accgctatgt tcaacggagg agtgtactac cactctaacg cagctcacaa ccttcttagc    1200
accatgaggt gggagtgat cagggagga tgcgaggttg agatctggaa gagggctcag      1260
aaggagaacg ttgagtacgt tagggatgga tctggacaaa gggtgatcag ggctggagag    1320
caaccaacca agatcccaga gccaatccca accgctgatg ctgcttga                 1368
```

<210> SEQ ID NO 3
<211> LENGTH: 2912
<212> TYPE: DNA
<213> ORGANISM: Artificial Sequence
<220> FEATURE:
<223> OTHER INFORMATION: The first plant transcription unit comprising
      Aspergillus nidulans delta 9 desaturase v3

<400> SEQUENCE: 3

```
ctcccagtat cattatagtg aaagttttgg ctctctcgcc ggtggttttt tacctctatt       60
taaaggggtt ttccacctaa aaattctggt atcattctca ctttacttgt tactttaatt     120
tctcataatc tttggttgaa attatcacgc ttccgcacac gatatcccta caatttatt      180
```

```
atttgttaaa cattttcaaa ccgcataaaa ttttatgaag tcccgtctat ctttaatgta      240
gtctaacatt ttcatattga aatatataat ttacttaatt ttagcgttgg tagaaagcat      300
aatgatttat tcttattctt cttcatataa atgtttaata tacaatataa acaaattctt      360
taccttaaga aggatttccc attttatatt ttaaaaatat atttatcaaa tatttttcaa      420
ccacgtaaat ctcataataa taagttgttt caaaagtaat aaaatttaac tccataattt      480
ttttattcga ctgatcttaa agcaacaccc agtgacacaa ctagccattt ttttctttga      540
ataaaaaaat ccaattatca ttgtattttt tttatacaat gaaaatttca ccaaacaatg      600
atttgtggta tttctgaagc aagtcatgtt atgcaaaatt ctataattcc catttgacac      660
tacggaagta actgaagatc tgcttttaca tgcgagacac atcttctaaa gtaattttaa      720
taatagttac tatattcaag atttcatata tcaaatactc aatattactt ctaaaaaatt      780
aattagatat aattaaaata ttactttttt aattttaagt ttaattgttg aatttgtgac      840
tattgattta ttattctact atgtttaaat tgttttatag atagtttaaa gtaaatataa      900
gtaatgtagt agagtgttag agtgttaccc taaaccataa actataagat ttatggtgga      960
ctaattttca tatatttctt attgctttta ccttttcttg gtatgtaagt ccgtaactgg     1020
aattactgtg ggttgccatg acactctgtg gtcttttggt tcatgcatgg atgcttgcgc     1080
aagaaaaaga caaagaacaa agaaaaaaga caaaacagag agacaaaacg caatcacaca     1140
accaactcaa attagtcact ggctgatcaa gatcgccgcg tccatgtatg tctaaatgcc     1200
atgcaaagca acacgtgctt aacatgcact ttaaatggct cacccatctc aacccacaca     1260
caaacacatt gccttttcct tcatcatcac cacaaccacc tgtatatatt cattctcttc     1320
cgccacctca atttcttcac ttcaacacac gtcaacctgc atatgcgtgt catcccatgc     1380
ccaaatctcc atgcatgttc caaccacctt ctctcttata taatacctat aaatacctct     1440
aatatcactc acttctttca tcatccatcc atccagagta ctactactct actactataa     1500 tacccccaacc caactcatat tcaatactac tctaggatcc aacaatgtct gctccaaccg     1560
ctgacatcag ggctagggct ccagaggcta agaaggttca catcgctgat accgctatca     1620
acaggcacaa ttggtacaag cacgtgaact ggctcaacgt cttcctcatc atcggaatcc     1680
cactctacgg atgcatccaa gctttctggg ttccacttca actcaagacc gctatctggg     1740
ctgtgatcta ctacttcttc accggacttg gaatcaccgc tggataccac aggctttggg     1800
ctcactgctc atactctgct actcttccac ttaggatctg gcttgctgct gttggaggag     1860
gagctgttga gggatctatc agatggtggg ctagggatca cagggctcat cataggtaca     1920
ccgataccga caaggaccca tactctgtta ggaagggact tctctactct caccttggat     1980
ggatggtgat gaagcagaac ccaaagagga tcggaaggac cgacatctct gatctcaacg     2040
aggacccagt tgttgtttgg caacacagga actacctcaa ggttgtgttc accatgggac     2100
ttgctgttcc aatgcttgtt gctggacttg atggggaga ttggcttgga ggattcgtgt     2160
acgctggaat ccttaggatc ttcttcgttc aacaagctac cttctgcgtg aactctcttg     2220
ctcactggct tggagatcaa ccattcgatg ataggaactc tcctagggat cacgtgatca     2280
ccgctcttgt tacccttgga gagggatacc acaaacttcca ccacgagttc catctgact      2340 acaggaacgc tatcgagtgg caccagtacg atcctaccaa gtggtctatc tgggcttgga     2400
agcaacttgg attggcttac gatctcaaga agttcagggc taacgagatc gagaagggaa     2460
gggttcaaca acttcagaag aagcttgata ggaagaggc tactcttgat tggggaaccc     2520
cacttgatca acttccagtg atggaatggg atgactacgt tgagcaagct aagaacggaa     2580
```

```
ggggacttgt tgctatcgct ggagttgttc acgatgttac cgacttcatc aaggatcacc    2640
caggaggaaa ggctatgatc tcttctggaa tcggaaagga tgctaccgct atgttcaacg    2700
gaggagtgta ctaccactct aacgcagctc acaaccttct tagcaccatg agggtgggag    2760
tgatcagggg aggatgcgag gttgagatct ggaagagggc tcagaaggag aacgttgagt    2820
acgttaggga tggatctgga caaagggtga tcagggctgg agagcaacca accaagatcc    2880
cagagccaat cccaaccgct gatgctgctt ga                                   2912

<210> SEQ ID NO 4
<211> LENGTH: 2517
<212> TYPE: DNA
<213> ORGANISM: Artificial Sequence
<220> FEATURE:
<223> OTHER INFORMATION: The second plant transcription unit comprising
      Aspergillus nidulans delta 9 desaturase v3

<400> SEQUENCE: 4
gaattcggaa atgggccaag tgaaatggaa atagagcttc aatccattta gtcccactca      60
aaatggtgct cgaattatat ttagttacgt tcgaatcaga caaccaagta tttggttaat     120
aaaaaccact cgcaacaaag gaaaacacc aagcgcgtgc gtccaacatc cgacggaagg      180
ggggtaatgt ggtccgaaaa ccttacaaaa atctgacgtc atctacccccc gaaaacgttg     240 aatcgtcaac gggggtagtt ttcgaattat ctttttttta ggggcagttt tattaatttg     300
ctctagaaat tttatgattt taattaaaaa agaaaaaga atatttgtat atttattttt     360
tatactcttt ttttgtccaa ctatttctct tattttggca actttaacta gactagtaac     420
ttatgtcaat gtgtatggat gcatgagagt gagtatacac atgtctaaat gcatgcctta     480
tgaaagcaac gcaccacaaa acgaagaccc ctttacaaat acatctcatc ccttagtacc     540
ctcttactac tgtcccgaca caaactcaaa acaaggtacc ctgcagggat ccaacaatgt     600
ctgctccaac cgctgacatc agggctaggg ctccagaggc taagaaggtt cacatcgctg     660
ataccgctat caacaggcac aattggtaca agcacgtgaa ctggctcaac gtcttcctca     720
tcatcggaat cccactctac ggatgcatcc aagctttctg ggttccactt caactcaaga     780
ccgctatctg ggctgtgatc tactacttct tcaccggact tggaatcacc gctggatacc     840
acaggctttg ggctcactgc tcatactctg ctactcttcc acttaggatc tggcttgctg     900
ctgttggagg aggagctgtt gagggatcta tcagatggtg ggctagggat cacgggctc     960 atcataggta caccgatacc gacaaggacc catactctgt taggaaggga cttctctact    1020
ctcaccttgg atggatggtg atgaagcaga acccaaagag gatcggaagg accgacatct    1080
ctgatctcaa cgaggaccca gttgttgttt ggcaacacag gaactacctc aaggttgtgt    1140
tcaccatggg acttgctgtt ccaatgcttg ttgctggact tggatgggga gattggcttg    1200
gaggattcgt gtacgctgga atccttagga tcttcttcgt tcaacaagct accttctgcg    1260
tgaactctct tgctcactgg cttggagatc aaccattcga tgataggaac tctcctaggg    1320
atcacgtgat caccgctctt gttacccttg agagggata ccacaacttc caccacgagt    1380
tcccatctga ctacaggaac gctatcgagt ggcaccagta cgatcctacc aagtggctga    1440
tctgggcttg gaagcaactt ggattggctt acgatctcaa gaagttcagg gctaacgaga    1500
tcgagaaggg aagggttcaa caacttcaga agaagcttga taggaagagg gctactcttg    1560
attggggaac cccacttgat caacttccag tgatggaatg ggatgactac gttgagcaag    1620
ctaagaacgg aaggggactt gttgctatcg ctggagttgt tcacgatgtt accgacttca    1680
```

```
tcaaggatca cccaggagga aaggctatga tctcttctgg aatcggaaag gatgctaccg    1740
ctatgttcaa cggaggagtg tactaccact ctaacgcagc tcacaacctt cttagcacca    1800
tgagggtggg agtgatcagg ggaggatgcg aggttgagat ctggaagagg gctcagaagg    1860
agaacgttga gtacgttagg gatggatctg gacaaagggt gatcagggct ggagagcaac    1920
caaccaagat cccagagcca atcccaaccg ctgatgctgc ttgagtagtt agcttaatca    1980
cctaggtcac cagcataatt tttattaatg tactaaatta ctgttttgtt aaatgcaatt    2040
ttgctttctc gggattttaa tatcaaaatc tatttagaaa tacacaatat tttgttgcag    2100
gcttgctgga gaatcgatct gctatcataa aaattacaaa aaaattttat ttgcctcaat    2160
tattttagga ttggtattaa ggacgcttaa attatttgtc gggtcactac gcatcattgt    2220
gattgagaag atcagcgata cgaaatattc gtagtactat cgataattta tttgaaaatt    2280
cataagaaaa gcaaacgtta catgaattga tgaaacaata caaagacaga taaagccacg    2340
cacatttagg atattggccg agattactga atattgagta agatcacgga atttctgaca    2400
ggagcatgtc ttcaattcag cccaaatggc agttgaaata ctcaaaccgc ccatatgca    2460 ggagcggatc attcattgtt tgtttggttg cctttgccaa catgggagtc caaggtt      2517
```

<210> SEQ ID NO 5
<211> LENGTH: 1828
<212> TYPE: DNA
<213> ORGANISM: Artificial Sequence
<220> FEATURE:
<223> OTHER INFORMATION: Plant transcription unit comprising
      phospinothricin acetyl transferase

<400> SEQUENCE: 5

```
cctgcaggga gattttcaa atcagtgcgc tagacgtgac gtaagtatcc gagtcagttt      60
ttatttttct actaatttgg tcgtttattt cggcgtgtag gacatggcaa ccgggcctga    120
atttcgcggg tattctgttt ctattccaac ttttcttga tccgcagcca ttaacgactt    180
ttgaatagat acgtctaggg tcgagggggg atccgtcgag ggggtccacc aaaaacgtaa    240
gcgcttacgt acatggtcga gggggtccac caaaaacgta agcgcttacg tacatggtcg    300
agggggtcca ccaaaaacgt aagcgcttac gtacatggtc gaggggtcc accaaaaacg    360 taagcgctta cgtacatggt cgactagagc gtgacgctcg cggtgacgcc atttcgcctt    420 tcagaaatg gataaatagc cttgcttcct attatatctt cccaaattac caatacatta    480
cactagcatc tgaatttcat aaccaatctc gatacaccaa atcgcagatc tggatcccaa    540
accatgtctc cggagaggag accagttgag attaggccag ctacagcagc tgatatggcc    600
gcggtttgtg atatcgttaa ccattacatt gagacgtcta cagtgaactt aggacagag    660 ccacaaacac cacaagagtg gattgatgat ctagagaggt tgcaagatag ataccctgg    720 ttggttgctg aggttgaggg tgttgtggct ggtattgctt acgctgggcc ctggaaggct    780
aggaacgctt acgattggac agttgagagt actgtttacg tgtcacatag gcatcaaagg    840
ttgggcctag gatctacatt gtacacacat ttgcttaagt ctatggaggc gcaaggtttt    900
aagtctgtgg ttgctgttat aggccttcca acgatccat ctgttaggtt gcatgaggct    960
ttgggataca cagcccgggg tacattgcgc gcagctggat acaagcatgg tggatggcat   1020
gatgttggtt tttggcaaag ggattttgag ttgccagctc ctccaaggcc agttaggcca   1080
gttacccaaa tctgagtagt tagcttaatc acctagagct cgatcggcgg caatagcttc   1140
ttagcgccat cccgggttga tcctatctgt gttgaaatag ttgcggtggg caaggctctc   1200
```

-continued

```
tttcagaaag acaggcggcc aaaggaaccc aagtgaggt gggctatggc tctcagttcc    1260
ttgtggaagc gcttggtcta aggtgcagag gtgttagcgg gatgaagcaa aagtgtccga    1320
ttgtaacaag atatgttgat cctacgtaag gatattaaag tatgtattca tcactaatat    1380
aatcagtgta ttccaatatg tactacgatt tccaatgtct ttattgtcgc cgtatgtaat    1440
cggcgtcaca aaataatccc cggtgacttt cttttaatcc aggatgaaat aatatgttat    1500
tataattttt gcgatttggt ccgttatagg aattgaagtg tgcttgaggt cggtcgccac    1560
cactcccatt tcataatttt acatgtattt gaaaataaa aatttatggt attcaattta    1620
aacacgtata cttgtaaaga atgatatctt gaaagaaata tagtttaaat atttattgat    1680
aaaataacaa gtcaggtatt atagtccaag caaaaacata aatttattga tgcaagttta    1740
aattcagaaa tatttcaata actgattata tcagctggta cattgccgta gatgaaagac    1800
tgagtgcgat attatggtgt aatacata                                       1828

<210> SEQ ID NO 6
<211> LENGTH: 29
<212> TYPE: DNA
<213> ORGANISM: Artificial Sequence
<220> FEATURE:
<223> OTHER INFORMATION: Patv5 forward primer

<400> SEQUENCE: 6
acaagagtgg attgatgatc tagagaggt                                      29

<210> SEQ ID NO 7
<211> LENGTH: 29
<212> TYPE: DNA
<213> ORGANISM: Artificial Sequence
<220> FEATURE:
<223> OTHER INFORMATION: patv5 reverse primer

<400> SEQUENCE: 7
ctttgatgcc tatgtgacac gtaaacagt                                      29

<210> SEQ ID NO 8
<211> LENGTH: 29
<212> TYPE: DNA
<213> ORGANISM: Artificial Sequence
<220> FEATURE:
<223> OTHER INFORMATION: pat v5 probe

<400> SEQUENCE: 8
ccagcgtaag caataccagc cacaacacc                                      29

<210> SEQ ID NO 9
<211> LENGTH: 23
<212> TYPE: DNA
<213> ORGANISM: Artificial Sequence
<220> FEATURE:
<223> OTHER INFORMATION: HMG1 forward primer

<400> SEQUENCE: 9
cctctctacc accgtctcac atg                                            23

<210> SEQ ID NO 10
<211> LENGTH: 20
<212> TYPE: DNA
<213> ORGANISM: Artificial Sequence
<220> FEATURE:
<223> OTHER INFORMATION: HMG1 reverse primer
```

<400> SEQUENCE: 10

```
gatctggccg gactgtttca                                                 20
```

<210> SEQ ID NO 11
<211> LENGTH: 25
<212> TYPE: DNA
<213> ORGANISM: Artificial Sequence
<220> FEATURE:
<223> OTHER INFORMATION: HMG1 probe

<400> SEQUENCE: 11

```
cgctcctcag ctaccacctc aacca                                           25
```

<210> SEQ ID NO 12
<211> LENGTH: 1523
<212> TYPE: DNA
<213> ORGANISM: Artificial Sequence
<220> FEATURE:
<223> OTHER INFORMATION: PCR amplified fragment of MgD9Ds

<400> SEQUENCE: 12

```
gaattcatgg cttcgtcatc ttcctccgtg ccggagttgg ctgccgcctt ccctgatggc     60
actaccgact tcaagcccat gaggaacacc aagggctacg acgtcagcaa gccgcacatt   120
tccgagacac ctatgacact caagaactgg cataagcacg tcaactggct caacaccacc   180
ttcatcttgt tgtgcccct ggctggtctc atatccactt actgggtccc tctgcagtgg    240
aagacggctg tatgggctgt cgtctactac ttcaacaccg gcctgggaat tactgccggt   300
aagtggctct tgaacaaacg agctaggccg ccgcccctgta ccaatcatc tgtatccatc   360
cctagatgct aactagaaaa cttgcgggtt accaccgact ttgggctcac agctcgtaca   420
aggcctcgct tccgctcaaa atctaccttg ccgccgttgg cgctggtgcc gtcgagggct   480
ccatcagatg gtggtccaac ggtcaccgcg cacaccaccg atacaccgat accgagaagg   540
accccctactc agtccgcaag ggtctcctgt actcacacat gggatggatg cttctgaagc   600
agaaccccaa gaagcagggc cgcaccgaca tcaccgacct gaacgaggac cccgttgtcg   660
tttggcagca ccgcaacttc ctcaagtgtg ttatcttcat ggccctcgtc ttccccacac   720
ttgtggctgg ccttggctgg ggtgactact ggggaggttt catctacgga ggtattctgc   780
gtgtcttctt cgtccagcag gccaccttct gcgtcaactc gcttgcccac tggctcggtg   840
accagccttt cgacgatcgc aactcgccgc gtgatcacgt catcacagcc ctggtcaccc   900
ttggagaggg ataccacaac ttccaccacg agttcccttc ggactaccgc aacgctattg   960
agtggtacca gtatgacccc accaagtggt caatctggat ctggaagcag cttggtcttg  1020
cccacaacct gaagcagttc cgccaaaacg agattgagaa gggacgcgtc cagcagctgc  1080
agaagaagct cgaccagaag cgcgccaagc ttgattgggg tattcccttg gagcagcttc  1140
ccgttgttag ctgggatgac tttgttgagc agtccaagaa cggaaaggct tggattgcag  1200
ttgccggtgt catccacgat gttggtgact catcaaggac ccaccctggt ggcagagctc  1260
tcatcaactc ggccattggc aaggacgcaa ccgcaatctt caacggcggt gtttacaacc  1320
actccaacgc cgctcacaac ctgctctcga ctatgcgtgt gggtgttttg cgtggcggct  1380
gcgaggttga gatctggaag cgcgcccagt ccgaaaacaa ggacgtctca accgtcgttg  1440
attcttcggg taaccgcatc gtccgcgcgg gtgggcaagc gaccaaggtc gtccagcctg  1500
ttccgggtgc tcaggccgcg tga                                          1523
```

<210> SEQ ID NO 13
<211> LENGTH: 1428
<212> TYPE: DNA
<213> ORGANISM: Artificial Sequence
<220> FEATURE:
<223> OTHER INFORMATION: Intronless MgD9Ds clone

<400> SEQUENCE: 13

| | | | | | |
|---|---|---|---|---|---|
| atggcttcgt | catcttcctc | cgtgccggag | ttggctgccg | ccttccctga | tggcactacc | 60 |
| gacttcaagc | ccatgaggaa | caccaagggc | tacgacgtca | gcaagccgca | catttccgag | 120 |
| acacctatga | cactcaagaa | ctggcataag | cacgtcaact | ggctcaacac | caccttcatc | 180 |
| ttgtttgtgc | ccctggctgg | tctcatatcc | acttactggg | tccctctgca | gtggaagacg | 240 |
| gctgtatggg | ctgtcgtcta | ctacttcaac | accggctgg | gaattactgc | cggttaccac | 300 |
| cgactttggg | ctcacagctc | gtacaaggcc | tcgcttccgc | tcaaaatcta | ccttgccgcc | 360 |
| gttggcgctg | gtgccgtcga | gggctccatc | agatggtggt | ccaacggtca | ccgcgcacac | 420 |
| caccgataca | ccgataccga | gaaggacccc | tactcagtcc | gcaagggtct | cctgtactca | 480 |
| cacatgggat | ggatgcttct | gaagcagaac | cccaagaagc | agggccgcac | cgacatcacc | 540 |
| gacctgaacg | aggaccccgt | tgtcgtttgg | cagcaccgca | acttcctcaa | gtgtgttatc | 600 |
| ttcatggccc | tcgtcttccc | cacacttgtg | gctggccttg | gctggggtga | ctactgggga | 660 |
| ggtttcatct | acgaggtat | tctgcgtgtc | ttcttcgtcc | agcaggccac | cttctgcgtc | 720 |
| aactcgcttg | cccactggct | cggtgaccag | cctttcgacg | atcgcaactc | gccgcgtgat | 780 |
| cacgtcatca | cagccctggt | caccccttgga | gagggatacc | acaacttcca | ccacgagttc | 840 |
| ccttcggact | accgcaacgc | tattgagtgg | taccagtatg | accccaccaa | gtggtcaatc | 900 |
| tggatctgga | agcagcttgg | tcttgcccac | aacctgaagc | agttccgcca | aaacgagatt | 960 |
| gagaagggac | gcgtccagca | gctgcagaag | aagctcgacc | agaagcgcgc | caagcttgat | 1020 |
| tgggggtattc | ccttggagca | gcttcccgtt | gttagctggg | atgactttgt | tgagcagtcc | 1080 |
| aagaacggaa | aggcttggat | tgcagttgcc | ggtgtcatcc | acgatgttgg | tgacttcatc | 1140 |
| aaggaccacc | ctggtggcag | agctctcatc | aactcggcca | ttgcaagga | cgcaaccgca | 1200 |
| atcttcaacg | gcgtgttta | caaccactcc | aacgccgctc | acaacctgct | ctcgactatg | 1260 |
| cgtgtgggtg | ttttgcgtgg | cggctgcgag | gttgagatct | ggaagcgcgc | ccagtccgaa | 1320 |
| aacaaggacg | tctcaaccgt | cgttgattct | tcgggtaacc | gcatcgtccg | cgcgggtggg | 1380 |
| caagcgacca | aggtcgtcca | gcctgttccg | ggtgctcagg | ccgcgtga | | 1428 |

<210> SEQ ID NO 14
<211> LENGTH: 1997
<212> TYPE: DNA
<213> ORGANISM: Leptosphaeria nodorum

<400> SEQUENCE: 14
cccgattcat taatgcagct ggcacgacag gtttcccgac tggaaagcgg gcagtgagcg 60
caacgcaatt aatgtgagtt agctcactca ttaggcaccc caggctttac actttatgct 120
tccggctcgt atgttgtgtg gaattgtgag cggataacaa tttcacacag gaaacagcta 180
tgaccatgat tacgccaagc tcgaaattaa ccctcactaa agggaacaaa agctggagct 240
ccaccgcggt ggcggccgct ctagaactag tggatccccc gggctgcagg aattcggcac 300
gagtatgcct tcccaccagg ctgttgctgg catgcaggcc atcgaccccg agtttgtcaa 360
gcagccgtct cctatggcga gcacctcgga gcccaaccgc aactccaagt acgatcctaa 420

```
gaagccgcac attacagaca tgcccatcac gcggtcaaac tggtaccagc atgtcaactg      480
gctcaacgtc atcttcatca tcggcgtgcc tctcgctggc tgcgtcgccg ccttctggac      540
ccctctgcag tggaagaccg ctgcgtgggc tgtcatctac tatttctgga ctggcctcgg      600
tatcaccgcc ggataccatc gtctctgggc acacaagtca tacaacgccg tcttcctct       660 gaggatctgg ctcgccgccg tcggcgctgg tgctgttgag ggttccatcc gctggtggag      720
ccgtgaccac cgcgcccacc accgctacac cgacaccaac aaggacccct acagtgtccg      780
caagggcctt ctctacagcc atctcggatg gatggtcatg aagcagaacc ccaagcgtat      840
cggccgcacc gacatcaccg acttgaacga ggaccccgtt gtcgtctggc agcacaagaa      900
ctacatcaag gccgtcgtca ccatgggctt gatctttccc tctgccgtcg ccggtctcat      960
gtggggcgat ggatgggtg gcttcatcta cgctggtatc ctccgtatct tcttcgtcca      1020
gcaggccacc ttctgcgtca actcgcttgc tcactggctc ggtgaccagc ccttcgacga     1080
ccgcaactct cctcgtgacc acgtcattac cgctcttgtc actctcggag agggctacca     1140
caacttccac cacgagttcc cctccgacta ccgcaacgcc atcgagtggc accagtacga     1200
ccctaccaag tggtccatct ggctgtggag caagctcggc ctcgcctcca acctcaagca     1260
gttccgctcc aacgaaatcg agaagggtcg tgtccagcag ctcagaaga agattgacca     1320 gaagcgcgcc aagctcgact ggggtgtccc tctcgaccag ctgcctgtca tagaatggga     1380
cgactatgtc gagcaggcca agaacggccg tggtctcatc gctgtcgctg tgtcgttca     1440 tgacgttacc gacttcatca acgagcaccc cggtggcaag acgcttatca agagcggcgt     1500
tggcaaggat gccaccgcca tgttcaacgg cggtgtctac ttccactcca acggagccca     1560
caacctcctt tctaccatga gggttggtgt catccgcggt ggctgtgaag ttgagatctg     1620
gaagcgcgct cagcgtgaga acaaggatgt cggtctggtc ctggacgacg caggcaaccc     1680
aatcatcagg gctggtaacc agattaccaa ggttgcgcaa cccattcaga gtgctagtgc     1740
agcatagatt ggatcttcat cttcacgagc gatgtatggc gtttggttgt ctctcttcct     1800
tggcggacag agtaatattc aatttcttag cgatcgttag aaagcatcat ggttacgatg     1860
ctcagtcatg ttagatggcg tatgtttgta gccttcctcg agtgattggs tatgaaaagt     1920
agcctcacgg cctagaccaa gaatgaaaac attcacgatt tcagaaaaaa aaaaaaaaa     1980 aaactcgagg gggggcc                                                    1997
```

<210> SEQ ID NO 15
<211> LENGTH: 1370
<212> TYPE: DNA
<213> ORGANISM: Leptosphaeria nodorum

<400> SEQUENCE: 15

```
ggatccatgg cggccttgga cagcattcca gaggataagg ctacctcgtc gaaatcgact       60
catattcaat atcaagaagt aacttttcgg aactggtata agaagataaa ttggctcaac      120
acgacgctgg tggtgctcat acccgctctt ggactctacc taacacgcac cacgccactt      180
acacgaccta cgctcatctg gtccgtcctg tactacttct gcacagcttt cggcatcaca      240
ggcggatatc atcgactatg gagtcatcgc agctactccg ctcgtctacc gctacgctta      300
ttcctagcct tcacaggcgc cggagccatc caaggtagtg ctcgatggtg gagcgcaaat      360
caccgcgccc accaccgatg gaccgacaca atgaaggacc cctactccgt tatgcgcggc      420
ctattattct cgcacatcgg atggatggta ttgaacagcg accccaaagt caaaggccga      480
acagacgtca gtgatctcga cagcgacccc gtcgtagtct ggcagcacaa gcactacggc      540
```

| | |
|---|---|
| aagtgcctgc tgttcgccgc gtggatattc cccatgatcg tagccggcct cggatgggga | 600 |
| gattggtggg gaggccttgt ctacgccggc atcattcgag cgtgtttcgt ccagcaggcg | 660 |
| acattttgcg tgaactctct cgcgcattgg atcggcgagc agccgttcga cgacagacgc | 720 |
| acgcctcgag accacgtttt gacagcgttg gtaacgatgg gagaaggata tcataacttc | 780 |
| caccacgaat tcccaagcga ttatcgcaac gcgatcatct ggtaccaata cgaccctacc | 840 |
| aaatggctca tttacctctt ctccctcggc cccttccccc tcgcatactc gctcaaaacc | 900 |
| ttccggtcca atgagattga aaagggcgg ttgcaacaac aacaaaaagc cctggacaag | 960 |
| aagcgctcag gacttgattg gggcctaccc ctcttccaac tccctgtcat atcgtgggac | 1020 |
| gacttccaag cgcgttgcaa agagtccggc gagatgctgg ttgctgtcgc aggtgtgatt | 1080 |
| cacgacgtca gccagtttat tgaagatcac cctggaggca ggagtttgat tcggagtgcg | 1140 |
| gtgggcaaag atgggacagg gatgtttaat ggaggcgtat atgagcacag taatgcggcg | 1200 |
| cataatctgt tgtcgacaat gagggtggga gtgcttagag gtgggcagga ggtggaggtg | 1260 |
| tggaagaagc agagagtgga tgttttaggg aagagcgaca ttttgagaca ggttacgcgg | 1320 |
| gtggagaggt tggttgaggg ggctgtggct gcgtagctaa ctgaccatgg | 1370 |

<210> SEQ ID NO 16
<211> LENGTH: 1428
<212> TYPE: DNA
<213> ORGANISM: Magnaporthe grisea

<400> SEQUENCE: 16

| | |
|---|---|
| atggcttcgt catcttcctc cgtgccggag ttggctgccg ccttccctga tggcactacc | 60 |
| gacttcaagc ccatgaggaa caccaagggc tacgacgtca gcaagccgca catttccgag | 120 |
| acacctatga cactcaagaa ctggcataag cacgtcaact ggctcaacac caccttcatc | 180 |
| ttgtttgtgc ccctggctgg tctcatatcc acttactggg tccctctgca gtggaagacg | 240 |
| gctgtatggc ctgtcgtcta ctacttcaac accggcctgg gaattactgc cggttaccac | 300 |
| cgactttggg ctcacagctc gtacaaggcc tcgcttccgc tcaaaatcta ccttgccgcc | 360 |
| gttggcgctg gtgccgtcga gggctccatc agatggtggt ccaacggtca ccgcgcacac | 420 |
| caccgataca ccgataccga aaggaccccc tactcagtcc gcaagggtct cctgtactca | 480 |
| cacatgggat ggatgcttct gaagcagaac cccaagaagc agggccgcac cgacatcacc | 540 |
| gacctgaacg aggaccccgt tgtcgtttgg cagcaccgca acttcctcaa gtgtgttatc | 600 |
| ttcatggccc tcgtcttccc cacacttgtg gctggccttg gctggggtga ctactgggga | 660 |
| ggtttcatct acggaggtat tctgcgtgtc ttcttcgtcc agcaggccac cttctgcgtc | 720 |
| aactcgcttg cccactggct cggtgaccag cctttcgacg atcgcaactc gccgcgtgat | 780 |
| cacgtcatca cagccctggt cacccttgga gagggatacc acaacttcca ccacgagttc | 840 |
| ccttcggact accgcaacgc tattgagtgg taccagtatg accccaccaa gtggtcaatc | 900 |
| tggatctgga agcagcttgg tcttgcccac aacctgaagc agttccgcca aaacgagatt | 960 |
| gagaagggac gcgtccagca gctgcagaag aagctcgacc agaagcgcgc caagcttgat | 1020 |
| tggggtattc ccttggagca gcttcccgtt gttagctggg atgactttgt tgagcagtcc | 1080 |
| aagaacggaa aggcttggat tgcagttgcc ggtgtcatcc acgatgttgg tgacttcatc | 1140 |
| aaggaccacc ctggtggcag agctctcatc aactcggcca ttggcaagga cgcaaccgca | 1200 |
| atcttcaacg gcggtgttta caaccactcc aacgccgctc acaacctgct ctcgactatg | 1260 |
| cgtgtgggtg ttttgcgtgg cggctgcgag gttgagatct ggaagcgcgc ccagtccgaa | 1320 |

| | |
|---|---|
| aacaaggacg tctcaaccgt cgttgattct tcgggtaacc gcatcgtccg cgcgggtggg | 1380 |
| caagcgacca aggtcgtcca gcctgttccg ggtgctcagg ccgcgtga | 1428 |

<210> SEQ ID NO 17
<211> LENGTH: 1062
<212> TYPE: DNA
<213> ORGANISM: Helicoverpa zea

<400> SEQUENCE: 17

| | |
|---|---|
| atggctccaa atatatcgga ggatgtgaac ggggtgctct tcgagagtga tgcagcgacg | 60 |
| ccggacctgg cgctgtccac gccgcctgtg cagaaggctg acaacaggcc caagcaactg | 120 |
| gtgtggagga acatactact gttcgcgtat cttcacttag cggctctttta cggaggttat | 180 |
| ctgttcctct tctcagctaa atggcagaca gacatatttg cctacatcct gtatgtgatc | 240 |
| tccgggcttg gtatcacggc tggagcacat cgcctgtggg cccacaagtc ctacaaagct | 300 |
| aaatggcctc tccgagttat cctggtcatc tttaacacag tggcattcca ggatgccgct | 360 |
| atggactggg cgcgcgacca ccgcatgcat cacaagtact cggaaaccga tgctgatcct | 420 |
| cataatgcga cccgaggatt cttcttctct cacattggct ggctgcttgt caggaaacat | 480 |
| cccgacctta aggagaaggg caagggactc gacatgagcg acttacttgc tgaccccatt | 540 |
| ctcaggttcc agaaaaaata ctacctgatc ctgatgccct tggcttgctt cgtgatgcct | 600 |
| accgtgattc ctgtgtactt ctggggtgaa acctggacca acgcattctt tgtggcggcc | 660 |
| atgttccgct acgcgttcat cctaaatgtg acgtggctcg tcaactctgc cgctcacaag | 720 |
| tggggagaca agcccctacga caaaagcatt aagccttccg aaaacttgtc ggtcgccatg | 780 |
| ttcgctctcg gagaaggatt ccacaactac caccacactt tcccttggga ctacaaaact | 840 |
| gctgagctgg gcaacaacaa actcaacttc actaccacct ttattaactt cttcgctaaa | 900 |
| attggctggg cttacgacct gaagacagtg tctgatgata tcgtcaagaa cagggtgaag | 960 |
| cgcactggtg acggctccca ccacctgtgg ggctggggag acgaaaatca atccaaagaa | 1020 |
| gaaattgatg ccgctatcag aatcaatcct aaggacgatt aa | 1062 |

<210> SEQ ID NO 18
<211> LENGTH: 1350
<212> TYPE: DNA
<213> ORGANISM: Leptosphaeria nodorum

<400> SEQUENCE: 18

| | |
|---|---|
| atggcggcct tggacagcat tccagaggat aaggctacct cgtcgaaatc gactcatatt | 60 |
| caatatcaag aagtaacttt tcggaactgg tataagaaga taaattggct caacacgacg | 120 |
| ctggtggtgc tcatacccgc tcttggactc tacctaacac gcaccacgcc acttacacga | 180 |
| cctacgctca tctggtccgt cctgtactac ttctgcacag ctttcggcat acaggcgga | 240 |
| tatcatcgac tatggagtca tcgcagctac tccgctcgtc taccgctacg cttattccta | 300 |
| gccttcacag gcgccggagc catccaaggt agtgctcgat ggtggagcgc aaatcaccgc | 360 |
| gcccaccacc gatggaccga cacaatgaag gaccccctact ccgttatgcg cggcctatta | 420 |
| ttctcgcaca tcgatggat ggtattgaac agcgacccca aagtcaaagg ccgaacagac | 480 |
| gtcagtgatc tcgacagcga ccccgtcgta gtctggcagc acaagcacta cggcaagtgc | 540 |
| ctgctgttcg ccgcgtggat attccccatg atcgtagccg gcctcggatg gggagattgg | 600 |
| tggggaggcc ttgtctacgc cggcatcatt cgagcgtgtt tcgtccagca ggcgacattt | 660 |
| tgcgtgaact ctctcgcgca ttggatcggc gagcagccgt tcgacgacag acgcacgcct | 720 |

```
cgagaccacg ttttgacagc gttggtaacg atgggagaag atatcataa cttccaccac    780
gaattcccaa gcgattatcg caacgcgatc atctggtacc aatacgaccc taccaaatgg    840
ctcatttacc tcttctccct cggccccttc cccctcgcat actcgctcaa aaccttccgg    900
tccaatgaga ttgaaaaagg gcggttgcaa caacaacaaa aagccctgga caagaagcgc    960
tcaggacttg attggggcct accCctcttc caactccctg tcatatcgtg ggacgacttc   1020
caagcgcgtt gcaaagagtc cggcgagatg ctggttgctg tcgcaggtgt gattcacgac   1080
gtcagccagt ttattgaaga tcaccctgga ggcaggagtt tgattcggag tgcggtgggc   1140
aaagatggga cagggatgtt taatggaggc gtatatgagc acagtaatgc ggcgcataat   1200
ctgttgtcga caatgagggt gggagtgctt agaggtgggc aggaggtgga ggtgtggaag   1260
aagcagagag tggatgtttt agggaagagc gacattttga gacaggttac gcgggtggag   1320
aggttggttg aggggctgt ggctgcgtag                                    1350

<210> SEQ ID NO 19
<211> LENGTH: 1428
<212> TYPE: DNA
<213> ORGANISM: Artificial Sequence
<220> FEATURE:
<223> OTHER INFORMATION: Canola-optimized desaturase sequence

<400> SEQUENCE: 19
atggccagca gttcttcaag tgtgccagaa cttgccgcag ctttccctga tgggacaacg     60
gacttcaaac ccatgaggaa caccaaaggc tatgatgtct ccaaacctca catctctgaa    120
acaccgatga ctttgaagaa ctggcacaaa catgtgaact ggctcaacac acattcatt    180
ctctttgttc cactggctgg gttgatctca acctattggg ttcctcttca atggaaaact    240
gcagtgtggg cagttgtgta ctacttcaac actggacttg ggatcactgc tggctaccat    300
agattgtggg cacattcctc ttacaaggcc agcttgcctc tcaaaatcta ccttgccgca    360
gttggtgctg gagccgttga aggttccata agatggtgga gcaacggaca cagagcacat    420
cacagataca cagacacaga gaaagatcct tactcagtga ggaagggatt gctctacagc    480
cacatgggtt ggatgctctt gaagcagaat ccaaagaagc aagggaggac ggacattact    540
gatctgaatg aggacccagt tgtggtctgg caacatagga actttctcaa gtgtgtgatc    600
ttcatggctt tggtctttcc caccccttgtt gctggcctgg gatggggaga ctactgggga    660
ggtttcatct atggagggat cttgagagtg ttctttgttc agcaagccac cttctgtgtc    720
aactcacttg cacattggct tggtgatcaa ccgtttgatg acagaaactc tccacgtgac    780
catgtcataa ctgctcttgt cacgctgggt gaaggctatc acaactttca ccatgagttt    840
ccgtcagact atagaaatgc gattgagtgg tatcagtatg accccacgaa gtggagcatt    900
tggatttgga agcaacttgg acttgctcac aatctcaagc agttcagaca gaatgagata    960
gagaagggaa gggttcaaca gttgcagaag aaactggatc agaagagagc gaaacttgat   1020
tggggaatac cgttggaaca actccctgtt gtgtcttggg atgactttgt tgaacagtca   1080
aagaatggca aggcatggat tgctgttgct ggtgtcattc acgatgttgg tgacttcatc   1140
aaggatcatc ctggtggacg tgctctcatc aactctgcga ttggcaaaga tgccacagcg   1200
atcttcaatg gaggtgtcta caatcattca aatgccgcac acaaccttct ctccaccatg   1260
agggttggtg tcctccgtgg agggtgcgaa gtggagatat ggaaacgtgc tcaaagtgag   1320
aacaaagatg tctctactgt ggttgatagt tctggcaacc gtattgtgag agctggtgga   1380
caagctacca agtggttca gccagtccct ggtgctcaag cagcttga                1428
```

<210> SEQ ID NO 20
<211> LENGTH: 1062
<212> TYPE: DNA
<213> ORGANISM: Artificial Sequence
<220> FEATURE:
<223> OTHER INFORMATION: Canola-optimized desaturase sequence

<400> SEQUENCE: 20

| | | | | | |
|---|---|---|---|---|---|
| atggctccca | acatttctga | ggatgtcaat | ggtgttcttt | ttgagtcaga | tgcggcaacc | 60 |
| cctgatttgg | ctctttccac | accacctgtg | caaaaagctg | acaacagacc | caagcaactt | 120 |
| gtgtggagga | acattttgct | tttcgcttac | ttgcacctcg | cagctctcta | cggaggctat | 180 |
| ttgtttctct | tcagtgcaaa | atggcagacc | gacattttcg | cttacattct | ttatgtcatc | 240 |
| tctggactgg | ggataactgc | tggggcacat | agactctggg | ctcacaagtc | atacaaagcc | 300 |
| aagtggccac | tcagagttat | actggtcatc | ttcaacacgg | ttgcctttca | agacgctgct | 360 |
| atggattggg | ctcgtgacca | tagaatgcat | cacaagtaca | gcgagaccga | cgcggaccca | 420 |
| cacaatgcaa | cgagaggttt | cttcttctct | cacattggct | ggcttcttgt | taggaaacat | 480 |
| cctgatctga | agaaaaaagg | gaagggactc | gacatgagtg | atctccttgc | tgatccaata | 540 |
| ctccgttttc | agaagaagta | ctatctgatc | ctcatgcctc | tggcctgttt | tgtgatgcca | 600 |
| accgttatcc | cggtttactt | tgggggagaa | acttggacaa | atgctttctt | cgtggcagcc | 660 |
| atgttccgtt | atgctttcat | cctgaatgtt | acctggttgg | tgaactctgc | cgcacacaag | 720 |
| tggggagaca | acccctatga | caagtccatc | aagccttccg | aaaaccttcc | agttgcgatg | 780 |
| tttgctttgg | gagaaggatt | tcacaattac | catcacactt | ttccgtggga | ctacaagaca | 840 |
| gcagagcttg | gaaacaacaa | gttgaacttc | acaacaacgt | tcatcaattt | ctttgcgaaa | 900 |
| atcggttggg | cctatgattt | gaagactgtg | agtgatgaca | ttgtcaagaa | cagggtcaag | 960 |
| agaactggcg | atggaagcca | tcatctctgg | ggctggggtg | atgagaatca | gagcaaagaa | 1020 |
| gagatagatg | cagccattag | gatcaaccct | aaagacgatt | ga | | 1062 |

<210> SEQ ID NO 21
<211> LENGTH: 1350
<212> TYPE: DNA
<213> ORGANISM: Artificial Sequence
<220> FEATURE:
<223> OTHER INFORMATION: Canola-optimized desaturase sequence

<400> SEQUENCE: 21

| | | | | | |
|---|---|---|---|---|---|
| atggctgcac | ttgatagcat | ccctgaggac | aaagcaacta | gctccaagtc | aacccacata | 60 |
| cagtaccaag | aggtcacgtt | taggaactgg | tacaagaaaa | tcaactggct | caacacgacc | 120 |
| cttgttgtcc | tcattcctgc | tcttgggttg | tacttgacga | gaaccacacc | tctcaccaga | 180 |
| cctaccctca | tttggtctgt | tctctactat | ttctgtacag | cgtttggcat | cactggtggc | 240 |
| taccacagac | tttggtccca | taggtcttac | agtgcgaggt | tgccattgag | actcttcctg | 300 |
| gctttcactg | gagctggtgc | gatccaaggt | tctgcaagat | ggtggtcagc | caatcatagg | 360 |
| gcacatcacc | gttggacgga | caccatgaag | gacccctact | ctgtgatgag | aggactgctg | 420 |
| ttctcccaca | taggttggat | ggttctcaac | tctgatccaa | aggtcaaagg | cagaacagat | 480 |
| gtttctgatc | ttgactctga | tcccgtcgtt | gtgtggcaac | acaaacacta | tggcaagtgt | 540 |
| ttgctctttg | ccgcttggat | ctttccgatg | atagtggctg | ggctggggtt | gggagattgg | 600 |
| tggggtggac | ttgtctatgc | tggcatcata | cgtgcctgct | tgttcagca | agccactttc | 660 |
| tgtgtcaact | cattggcaca | ttggataggt | gaacaaccgt | ttgatgacag | acgtactcca | 720 |

-continued

| | |
|---|---|
| agggatcatg ttctgactgc gttggtcaca atgggagaag gataccacaa cttccaccat | 780 |
| gagtttccga gtgactacag aaatgccatc atttggtatc agtatgaccc tacaaagtgg | 840 |
| ctcatctatc tcttcagctt gggtcccttc ccattggcct actctctcaa gaccttccgt | 900 |
| tccaatgaga ttgagaaagg aaggcttcag caacagcaaa aggctcttga caagaaaaga | 960 |
| agtggtcttg attggggact tcctctcttc cagcttccag tgatctcatg ggatgacttt | 1020 |
| caagctcgtt gcaaagaaag tggagagatg cttgttgctg ttgctggagt gatccatgat | 1080 |
| gtctcccagt tcattgaaga tcatcctggt gggaggagcc tcattagaag tgctgttggg | 1140 |
| aaagatggga ctggcatgtt caatggtgga gtgtatgaac attcaaacgc cgcacacaac | 1200 |
| ttgctgagca caatgagagt tggagtcttg agaggtggac aagaagtgga ggtttggaag | 1260 |
| aaacagaggg tggatgttct tgggaagtca gacattcttc gtcaagtgac aagggtggag | 1320 |
| cgtctggtgg aaggagctgt tgcagcgtga | 1350 |

<210> SEQ ID NO 22
<211> LENGTH: 1350
<212> TYPE: DNA
<213> ORGANISM: Artificial Sequence
<220> FEATURE:
<223> OTHER INFORMATION: Canola-optimized desaturase

<400> SEQUENCE: 22

| | |
|---|---|
| atggctgctc ttgattctat cccagaggat aaggctacct cttctaagtc tacccacatc | 60 |
| caataccaag aagttacctt caggaactgg tacaagaaga tcaactggct taacaccacc | 120 |
| cttgttgttc ttatcccagc tcttggactt taccttacca ggaccacccc acttaccagg | 180 |
| ccaaccctta tctggtctgt tctttactac ttctgcaccg ctttcggaat aaccggagga | 240 |
| taccacaggc tttggtctca caggtcttac tctgctaggc ttccacttag gcttttcctt | 300 |
| gctttcaccg gagctggagc tatccaagga tctgctagat ggtggtctgc taaccacagg | 360 |
| gctcaccaca ggtggaccga taccatgaag gacccatact ctgttatgag gggacttctt | 420 |
| ttctctcaca tcggatggat ggttcttaac tctgatccaa aggttaaggg aaggaccgat | 480 |
| gtttctgatc ttgattctga tccagttgtt gtttggcaac acaagcacta cggaaagtgc | 540 |
| cttcttttcg ctgcttggat cttcccaatg atcgttgctg acttggatg gggagattgg | 600 |
| tggggaggac ttgtttacgc tggaatcatc agggcttgct tcgttcaaca agctaccttc | 660 |
| tgcgttaact ctcttgctca ctggatcgga gagcaaccat cgacgatag gaggacccca | 720 |
| agggatcacg ttcttaccgc tcttgttacc atgggagagg gataccacaa cttccaccac | 780 |
| gagttcccat ctgattacag gaacgctatc atctggtacc aatacgatcc aaccaagtgg | 840 |
| cttatctacc ttttctctct tggaccattc ccacttgctt actctcttaa gaccttcagg | 900 |
| tctaacgaga tcgagaaggg aaggcttcaa caacaacaaa aggctcttga taagaagagg | 960 |
| tctggacttg attggggact tccactttc caacttccag ttatctcttg ggatgatttc | 1020 |
| caagctaggt gcaaggagtc tggagagatg cttgttgctg ttgctggagt tatccacgat | 1080 |
| gtttctcaat tcatcgagga tcacccagga ggaaggctc ttatcaggtc tgctgttgga | 1140 |
| aaggatggaa ccggaatgtt caacggagga gtttacgagc actctaacgc tgctcacaac | 1200 |
| cttctttcta ccatgagggt tggagttctt aggggaggac aagaggttga ggtttggaag | 1260 |
| aagcaaaggg ttgatgttct tggaaagtca gatatcctta ggcaagttac cagggttgag | 1320 |
| aggcttgttg agggagctgt tgctgcttga | 1350 |

<210> SEQ ID NO 23
<211> LENGTH: 1062
<212> TYPE: DNA
<213> ORGANISM: Artificial Sequence
<220> FEATURE:
<223> OTHER INFORMATION: Canola-optimized desaturase

<400> SEQUENCE: 23

```
atggctccaa acatctctga ggatgttaac ggagttcttt tcgagtctga tgctgctacc        60
ccagatcttg ctctttctac cccaccagtt caaaaggctg ataacaggcc aaagcaactt       120
gtttggagga acatccttct tttcgcttac cttcaccttg ctgctcttta cggaggatac       180
cttttccttt tctctgctaa gtggcaaacc gatatcttcg cttacatcct ttacgttatc       240
tctggacttg aataaccgc tggagcacac aggctttggg ctcacaagtc ttacaaggct       300
aagtggccac ttagggttat ccttgttatc ttcaacaccg ttgctttcca agacgctgct       360
atggattggg ctagggatca caggatgcac acaagtact ctgagaccga cgctgatcca       420
cacaacgcta ccaggggatt cttcttctct cacatcggat ggcttcttgt taggaagcac       480
ccagatctta aggagaaggg aaagggactt gatatgtctg atcttcttgc tgatccaatc       540
cttaggttcc aaaagaagta ctaccttatc cttatgccac ttgcttgctt cgttatgcca       600
accgttatcc cagtttactt ctggggagag acctggacca acgctttctt cgttgctgct       660
atgttcaggt acgctttcat ccttaacgtt acctggcttg ttaactctgc tgctcacaag       720
tggggagata agccatacga taagtctatc aagccatctg agaacctttc tgttgctatg       780
ttcgctcttg agagggatt ccacaactac caccacacct tcccatggga ttacaagacc       840
gctgagcttg aaacaacaa gcttaacttc accaccacct tcatcaactt cttcgctaag       900
atcggatggg cttacgatct taagaccgtt tctgatgata tcgttaagaa cagggttaag       960
aggaccggag atggatcaca ccacctttgg ggatggggag atgagaacca atctaaggag      1020
gagatcgatg ctgctatcag gatcaaccca aaggatgatt ga                         1062
```

<210> SEQ ID NO 24
<211> LENGTH: 1368
<212> TYPE: DNA
<213> ORGANISM: Aspergillus nidulans

<400> SEQUENCE: 24

```
atgtctgctc caaccgctga catcagggct agggctccag aggctaagaa ggttcacatc        60
gctgataccg ctatcaacag gcacaattgg tacaagcacg tgaactggct caacgtcttc       120
ctcatcatcg gaatcccact ctacggatgc atccaagctt tctgggttcc acttcaactc       180
aagaccgcta tctgggctgt gatctactac ttcttcaccg gacttggaat caccgctgga       240
taccacaggc tttgggctca ctgctcttac tctgctactc ttccacttag gatctggctt       300
gctgctgttg gaggaggagc tgttgaggga tctatcagat ggtgggctag ggatcacagg       360
gctcatcata ggtacaccga taccgacaag gaccctatact ctgttaggaa gggacttctc       420
tactctcacc ttggatggat ggtgatgaag cagaacccaa gaggatcgg aaggaccgac       480
atctctgatc tcaacgagga cccagttgtt gtttggcaac acaggaacta cctcaaggtt       540
gtgttcacca tgggacttgc tgttccaatg cttgttgctg acttggatg gggagattgg       600
cttggaggat tcgtgtacgc tggaatcctt aggatcttct tcgttcaaca agctaccttc       660
tgcgtgaact ctcttgctca ctggcttgga gatcaaccat tcgatgatag gaactctcct       720
agggatcacg tgatcaccgc tcttgttacc cttggagagg gataccacaa cttccaccac       780
```

```
gagttcccat ctgactacag gaacgctatc gagtggcacc agtacgatcc taccaagtgg      840
tctatctggg cttggaagca acttggattg gcttacgatc tcaagaagtt cagggctaac      900
gagatcgaga agggaagggt tcaacaactt cagaagaagc ttgataggaa gagggctact      960
cttgattggg gaaccccact tgatcaactt ccagtgatgg aatgggatga ctacgttgag     1020
caagctaaga acgaagggg acttgttgct atcgctggag ttgttcacga tgttaccgac     1080
ttcatcaagg atcacccagg aggaaaggct atgatctctt ctggaatcgg aaaggatgct     1140
accgctatgt tcaacggagg agtgtactac cactctaacg cagctcacaa ccttcttagc     1200
accatgaggg tgggagtgat caggggagga tgcgaggttg agatctggaa gagggctcag     1260
aaggagaacg ttgagtacgt tagggatgga tctggacaaa gggtgatcag ggctggagag     1320
caaccaacca agatcccaga gccaatccca accgctgatg ctgcttga                  1368
```

<210> SEQ ID NO 25
<211> LENGTH: 1368
<212> TYPE: DNA
<213> ORGANISM: Artificial Sequence
<220> FEATURE:
<223> OTHER INFORMATION: AnD9DS v3 silent mutant

<400> SEQUENCE: 25

```
atgtctgctc caaccgctga catcagggct agggctccag aggctaagaa ggttcacatc       60
gctgataccg ctatcaacag gcacaattgg tacaagcacg tgaactggct caacgtcttc      120
ctcatcatcg gaatcccact ctacggatgc atccaagctt tctgggttcc acttcaactc      180
aagaccgcta tctgggctgt gatctactac ttcttcaccg acttggaat caccgctgga       240 taccacaggc tttgggctca ctgctcatac tctgctactc ttccacttag gatctggctt      300
gctgctgttg gaggaggagc tgttgaggga tctatcagat ggtgggctag ggatcacagg      360
gctcatcata ggtacaccga taccgacaag gacccatact ctgttaggaa gggacttctc      420
tactctcacc ttggatggat ggtgatgaag cagaacccaa agaggatcgg aaggaccgac      480
atctctgatc tcaacgagga cccagttgtt gtttggcaac acaggaacta cctcaaggtt      540
gtgttcacca tgggacttgc tgttccaatg cttgttgctg acttggatg gggagattgg       600 cttggaggat tcgtgtacgc tggaatcctt aggatcttct tcgttcaaca agctaccttc      660
tgcgtgaact ctcttgctca ctggcttgga gatcaaccat tcgatgatag gaactctcct      720
agggatcacg tgatcaccgc tcttgttacc cttggagagg gataccacaa cttccaccac      780
gagttcccat ctgactacag gaacgctatc gagtggcacc agtacgatcc taccaagtgg      840
tctatctggg cttggaagca acttggattg gcttacgatc tcaagaagtt cagggctaac      900
gagatcgaga agggaagggt tcaacaactt cagaagaagc ttgataggaa gagggctact      960
cttgattggg gaaccccact tgatcaactt ccagtgatgg aatgggatga ctacgttgag     1020
caagctaaga acgaagggg acttgttgct atcgctggag ttgttcacga tgttaccgac     1080
ttcatcaagg atcacccagg aggaaaggct atgatctctt ctggaatcgg aaaggatgct     1140
accgctatgt tcaacggagg agtgtactac cactctaacg cagctcacaa ccttcttagc     1200
accatgaggg tgggagtgat caggggagga tgcgaggttg agatctggaa gagggctcag     1260
aaggagaacg ttgagtacgt tagggatgga tctggacaaa gggtgatcag ggctggagag     1320
caaccaacca agatcccaga gccaatccca accgctgatg ctgcttga                  1368
```

-continued

<210> SEQ ID NO 26
<211> LENGTH: 475
<212> TYPE: PRT
<213> ORGANISM: Magnaporthe grisea

<400> SEQUENCE: 26

Met Ala Ser Ser Ser Ser Ser Val Pro Glu Leu Ala Ala Ala Phe Pro
1               5                   10                  15

Asp Gly Thr Thr Asp Phe Lys Pro Met Arg Asn Thr Lys Gly Tyr Asp
            20                  25                  30

Val Ser Lys Pro His Ile Ser Glu Thr Pro Met Thr Leu Lys Asn Trp
        35                  40                  45

His Lys His Val Asn Trp Leu Asn Thr Thr Phe Ile Leu Phe Val Pro
    50                  55                  60

Leu Ala Gly Leu Ile Ser Thr Tyr Trp Val Pro Leu Gln Trp Lys Thr
65                  70                  75                  80

Ala Val Trp Ala Val Val Tyr Tyr Phe Asn Thr Gly Leu Gly Ile Thr
                85                  90                  95

Ala Gly Tyr His Arg Leu Trp Ala His Ser Ser Tyr Lys Ala Ser Leu
            100                 105                 110

Pro Leu Lys Ile Tyr Leu Ala Ala Val Gly Ala Gly Ala Val Glu Gly
        115                 120                 125

Ser Ile Arg Trp Trp Ser Asn Gly His Arg Ala His His Arg Tyr Thr
    130                 135                 140

Asp Thr Glu Lys Asp Pro Tyr Ser Val Arg Lys Gly Leu Leu Tyr Ser
145                 150                 155                 160

His Met Gly Trp Met Leu Leu Lys Gln Asn Pro Lys Lys Gln Gly Arg
                165                 170                 175

Thr Asp Ile Thr Asp Leu Asn Glu Asp Pro Val Val Val Trp Gln His
            180                 185                 190

Arg Asn Phe Leu Lys Cys Val Ile Phe Met Ala Leu Val Phe Pro Thr
        195                 200                 205

Leu Val Ala Gly Leu Gly Trp Gly Asp Tyr Trp Gly Gly Phe Ile Tyr
    210                 215                 220

Gly Gly Ile Leu Arg Val Phe Phe Val Gln Gln Ala Thr Phe Cys Val
225                 230                 235                 240

Asn Ser Leu Ala His Trp Leu Gly Asp Gln Pro Phe Asp Asp Arg Asn
                245                 250                 255

Ser Pro Arg Asp His Val Ile Thr Ala Leu Val Thr Leu Gly Glu Gly
            260                 265                 270

Tyr His Asn Phe His His Glu Phe Pro Ser Asp Tyr Arg Asn Ala Ile
        275                 280                 285

Glu Trp Tyr Gln Tyr Asp Pro Thr Lys Trp Ser Ile Trp Ile Trp Lys
    290                 295                 300

Gln Leu Gly Leu Ala His Asn Leu Lys Gln Phe Arg Gln Asn Glu Ile
305                 310                 315                 320

Glu Lys Gly Arg Val Gln Gln Leu Gln Lys Lys Leu Asp Gln Lys Arg
                325                 330                 335

Ala Lys Leu Asp Trp Gly Ile Pro Leu Glu Gln Leu Pro Val Val Ser
            340                 345                 350

Trp Asp Asp Phe Val Glu Gln Ser Lys Asn Gly Lys Ala Trp Ile Ala
        355                 360                 365

Val Ala Gly Val Ile His Asp Val Gly Asp Phe Ile Lys Asp His Pro
    370                 375                 380

```
Gly Gly Arg Ala Leu Ile Asn Ser Ala Ile Gly Lys Asp Ala Thr Ala
385                 390                 395                 400

Ile Phe Asn Gly Gly Val Tyr Asn His Ser Asn Ala Ala His Asn Leu
                405                 410                 415

Leu Ser Thr Met Arg Val Gly Val Leu Arg Gly Gly Cys Glu Val Glu
            420                 425                 430

Ile Trp Lys Arg Ala Gln Ser Glu Asn Lys Asp Val Ser Thr Val Val
        435                 440                 445

Asp Ser Ser Gly Asn Arg Ile Val Arg Ala Gly Gly Gln Ala Thr Lys
    450                 455                 460

Val Val Gln Pro Val Pro Gly Ala Gln Ala Ala
465                 470                 475

<210> SEQ ID NO 27
<211> LENGTH: 353
<212> TYPE: PRT
<213> ORGANISM: Helicoverpa zea

<400> SEQUENCE: 27

Met Ala Pro Asn Ile Ser Glu Asp Val Asn Gly Val Leu Phe Glu Ser
1               5                   10                  15

Asp Ala Ala Thr Pro Asp Leu Ala Leu Ser Thr Pro Val Gln Lys
                20                  25                  30

Ala Asp Asn Arg Pro Lys Gln Leu Val Trp Arg Asn Ile Leu Leu Phe
            35                  40                  45

Ala Tyr Leu His Leu Ala Leu Tyr Gly Gly Tyr Leu Phe Leu Phe
    50                  55                  60

Ser Ala Lys Trp Gln Thr Asp Ile Phe Ala Tyr Ile Leu Tyr Val Ile
65                  70                  75                  80

Ser Gly Leu Gly Ile Thr Ala Gly Ala His Arg Leu Trp Ala His Lys
                85                  90                  95

Ser Tyr Lys Ala Lys Trp Pro Leu Arg Val Ile Leu Val Ile Phe Asn
            100                 105                 110

Thr Val Ala Phe Gln Asp Ala Ala Met Asp Trp Ala Arg Asp His Arg
        115                 120                 125

Met His His Lys Tyr Ser Glu Thr Asp Ala Asp Pro His Asn Ala Thr
    130                 135                 140

Arg Gly Phe Phe Phe Ser His Ile Gly Trp Leu Leu Val Arg Lys His
145                 150                 155                 160

Pro Asp Leu Lys Glu Lys Gly Lys Gly Leu Asp Met Ser Asp Leu Leu
                165                 170                 175

Ala Asp Pro Ile Leu Arg Phe Gln Lys Lys Tyr Tyr Leu Ile Leu Met
            180                 185                 190

Pro Leu Ala Cys Phe Val Met Pro Thr Val Ile Pro Val Tyr Phe Trp
        195                 200                 205

Gly Glu Thr Trp Thr Asn Ala Phe Phe Val Ala Ala Met Phe Arg Tyr
    210                 215                 220

Ala Phe Ile Leu Asn Val Thr Trp Leu Val Asn Ser Ala Ala His Lys
225                 230                 235                 240

Trp Gly Asp Lys Pro Tyr Asp Lys Ser Ile Lys Pro Ser Glu Asn Leu
                245                 250                 255

Ser Val Ala Met Phe Ala Leu Gly Glu Gly Phe His Asn Tyr His His
            260                 265                 270

Thr Phe Pro Trp Asp Tyr Lys Thr Ala Glu Leu Gly Asn Asn Lys Leu
        275                 280                 285
```

-continued

```
Asn Phe Thr Thr Thr Phe Ile Asn Phe Phe Ala Lys Ile Gly Trp Ala
    290                 295                 300

Tyr Asp Leu Lys Thr Val Ser Asp Asp Ile Val Lys Asn Arg Val Lys
305                 310                 315                 320

Arg Thr Gly Asp Gly Ser His His Leu Trp Gly Trp Gly Asp Glu Asn
                325                 330                 335

Gln Ser Lys Glu Glu Ile Asp Ala Ala Ile Arg Ile Asn Pro Lys Asp
            340                 345                 350

Asp

<210> SEQ ID NO 28
<211> LENGTH: 449
<212> TYPE: PRT
<213> ORGANISM: Leptosphaeria nodorum

<400> SEQUENCE: 28

Met Ala Ala Leu Asp Ser Ile Pro Glu Asp Lys Ala Thr Ser Ser Lys
1               5                   10                  15

Ser Thr His Ile Gln Tyr Gln Glu Val Thr Phe Arg Asn Trp Tyr Lys
            20                  25                  30

Lys Ile Asn Trp Leu Asn Thr Thr Leu Val Val Leu Ile Pro Ala Leu
        35                  40                  45

Gly Leu Tyr Leu Thr Arg Thr Thr Pro Leu Thr Arg Pro Thr Leu Ile
    50                  55                  60

Trp Ser Val Leu Tyr Tyr Phe Cys Thr Ala Phe Gly Ile Thr Gly Gly
65                  70                  75                  80

Tyr His Arg Leu Trp Ser His Arg Ser Tyr Ser Ala Arg Leu Pro Leu
                85                  90                  95

Arg Leu Phe Leu Ala Phe Thr Gly Ala Gly Ala Ile Gln Gly Ser Ala
            100                 105                 110

Arg Trp Trp Ser Ala Asn His Arg Ala His His Arg Trp Thr Asp Thr
        115                 120                 125

Met Lys Asp Pro Tyr Ser Val Met Arg Gly Leu Leu Phe Ser His Ile
    130                 135                 140

Gly Trp Met Val Leu Asn Ser Asp Pro Lys Val Lys Gly Arg Thr Asp
145                 150                 155                 160

Val Ser Asp Leu Asp Ser Asp Pro Val Val Val Trp Gln His Lys His
                165                 170                 175

Tyr Gly Lys Cys Leu Leu Phe Ala Ala Trp Ile Phe Pro Met Ile Val
            180                 185                 190

Ala Gly Leu Gly Trp Gly Asp Trp Trp Gly Gly Leu Val Tyr Ala Gly
        195                 200                 205

Ile Ile Arg Ala Cys Phe Val Gln Gln Ala Thr Phe Cys Val Asn Ser
    210                 215                 220

Leu Ala His Trp Ile Gly Glu Gln Pro Phe Asp Asp Arg Arg Thr Pro
225                 230                 235                 240

Arg Asp His Val Leu Thr Ala Leu Val Thr Met Gly Glu Gly Tyr His
                245                 250                 255

Asn Phe His His Glu Phe Pro Ser Asp Tyr Arg Asn Ala Ile Ile Trp
            260                 265                 270

Tyr Gln Tyr Asp Pro Thr Lys Trp Leu Ile Tyr Leu Phe Ser Leu Gly
        275                 280                 285

Pro Phe Pro Leu Ala Tyr Ser Leu Lys Thr Phe Arg Ser Asn Glu Ile
    290                 295                 300
```

```
Glu Lys Gly Arg Leu Gln Gln Gln Lys Ala Leu Asp Lys Lys Arg
305                 310                 315                 320

Ser Gly Leu Asp Trp Gly Leu Pro Leu Phe Gln Leu Pro Val Ile Ser
            325                 330                 335

Trp Asp Asp Phe Gln Ala Arg Cys Lys Glu Ser Gly Glu Met Leu Val
                340                 345                 350

Ala Val Ala Gly Val Ile His Asp Val Ser Gln Phe Ile Glu Asp His
            355                 360                 365

Pro Gly Gly Arg Ser Leu Ile Arg Ser Ala Val Gly Lys Asp Gly Thr
    370                 375                 380

Gly Met Phe Asn Gly Gly Val Tyr Glu His Ser Asn Ala Ala His Asn
385                 390                 395                 400

Leu Leu Ser Thr Met Arg Val Gly Val Leu Arg Gly Gly Gln Glu Val
                405                 410                 415

Glu Val Trp Lys Lys Gln Arg Val Asp Val Leu Gly Lys Ser Asp Ile
            420                 425                 430

Leu Arg Gln Val Thr Arg Val Glu Arg Leu Val Glu Gly Ala Val Ala
                435                 440                 445

Ala
```

<210> SEQ ID NO 29
<211> LENGTH: 455
<212> TYPE: PRT
<213> ORGANISM: Aspergillus nidulans

<400> SEQUENCE: 29

```
Met Ser Ala Pro Thr Ala Asp Ile Arg Ala Arg Ala Pro Glu Ala Lys
1               5                   10                  15

Lys Val His Ile Ala Asp Thr Ala Ile Asn Arg His Asn Trp Tyr Lys
                20                  25                  30

His Val Asn Trp Leu Asn Val Phe Leu Ile Gly Ile Pro Leu Tyr
            35                  40                  45

Gly Cys Ile Gln Ala Phe Trp Val Pro Leu Gln Leu Lys Thr Ala Ile
    50                  55                  60

Trp Ala Val Ile Tyr Tyr Phe Phe Thr Gly Leu Gly Ile Thr Ala Gly
65                  70                  75                  80

Tyr His Arg Leu Trp Ala His Cys Ser Tyr Ser Ala Thr Leu Pro Leu
                85                  90                  95

Arg Ile Trp Leu Ala Ala Val Gly Gly Ala Val Glu Gly Ser Ile
            100                 105                 110

Arg Trp Trp Ala Arg Asp His Arg Ala His His Arg Tyr Thr Asp Thr
    115                 120                 125

Asp Lys Asp Pro Tyr Ser Val Arg Lys Gly Leu Leu Tyr Ser His Leu
130                 135                 140

Gly Trp Met Val Met Lys Gln Asn Pro Lys Arg Ile Gly Arg Thr Asp
145                 150                 155                 160

Ile Ser Asp Leu Asn Glu Asp Pro Val Val Trp Gln His Arg Asn
                165                 170                 175

Tyr Leu Lys Val Val Phe Thr Met Gly Leu Ala Val Pro Met Leu Val
            180                 185                 190

Ala Gly Leu Gly Trp Gly Asp Trp Leu Gly Gly Phe Val Tyr Ala Gly
    195                 200                 205

Ile Leu Arg Ile Phe Phe Val Gln Gln Ala Thr Phe Cys Val Asn Ser
    210                 215                 220
```

```
Leu Ala His Trp Leu Gly Asp Gln Pro Phe Asp Asp Arg Asn Ser Pro
225                 230                 235                 240

Arg Asp His Val Ile Thr Ala Leu Val Thr Leu Gly Glu Gly Tyr His
            245                 250                 255

Asn Phe His His Glu Phe Pro Ser Asp Tyr Arg Asn Ala Ile Glu Trp
                260                 265                 270

His Gln Tyr Asp Pro Thr Lys Trp Ser Ile Trp Ala Trp Lys Gln Leu
            275                 280                 285

Gly Leu Ala Tyr Asp Leu Lys Lys Phe Arg Ala Asn Glu Ile Glu Lys
            290                 295                 300

Gly Arg Val Gln Gln Leu Gln Lys Lys Leu Asp Arg Lys Arg Ala Thr
305                 310                 315                 320

Leu Asp Trp Gly Thr Pro Leu Asp Gln Leu Pro Val Met Glu Trp Asp
                325                 330                 335

Asp Tyr Val Glu Gln Ala Lys Asn Gly Arg Gly Leu Val Ala Ile Ala
                340                 345                 350

Gly Val Val His Asp Val Thr Asp Phe Ile Lys Asp His Pro Gly Gly
            355                 360                 365

Lys Ala Met Ile Ser Ser Gly Ile Gly Lys Asp Ala Thr Ala Met Phe
370                 375                 380

Asn Gly Gly Val Tyr Tyr His Ser Asn Ala Ala His Asn Leu Leu Ser
385                 390                 395                 400

Thr Met Arg Val Gly Val Ile Arg Gly Gly Cys Glu Val Glu Ile Trp
                405                 410                 415

Lys Arg Ala Gln Lys Glu Asn Val Glu Tyr Val Arg Asp Gly Ser Gly
            420                 425                 430

Gln Arg Val Ile Arg Ala Gly Glu Gln Pro Thr Lys Ile Pro Glu Pro
            435                 440                 445

Ile Pro Thr Ala Asp Ala Ala
            450                 455

<210> SEQ ID NO 30
<211> LENGTH: 455
<212> TYPE: PRT
<213> ORGANISM: Aspergillus nidulans

<400> SEQUENCE: 30

Met Ser Ala Pro Thr Ala Asp Ile Arg Ala Arg Ala Pro Glu Ala Lys
1               5                   10                  15

Lys Val His Ile Ala Asp Thr Ala Ile Asn Arg His Asn Trp Tyr Lys
            20                  25                  30

His Val Asn Trp Leu Asn Val Phe Leu Ile Ile Gly Ile Pro Leu Tyr
        35                  40                  45

Gly Cys Ile Gln Ala Phe Trp Val Pro Leu Gln Leu Lys Thr Ala Ile
    50                  55                  60

Trp Ala Val Ile Tyr Tyr Phe Phe Thr Gly Leu Gly Ile Thr Ala Gly
65                  70                  75                  80

Tyr His Arg Leu Trp Ala His Cys Ser Tyr Ser Ala Thr Leu Pro Leu
                85                  90                  95

Arg Ile Trp Leu Ala Ala Val Gly Gly Ala Val Glu Gly Ser Ile
            100                 105                 110

Arg Trp Trp Ala Arg Asp His Arg Ala His His Arg Tyr Thr Asp Thr
        115                 120                 125

Asp Lys Asp Pro Tyr Ser Val Arg Lys Gly Leu Leu Tyr Ser His Leu
    130                 135                 140
```

Gly Trp Met Val Met Lys Gln Asn Pro Lys Arg Ile Gly Arg Thr Asp
145                 150                 155                 160

Ile Ser Asp Leu Asn Glu Asp Pro Val Val Trp Gln His Arg Asn
            165                 170                 175

Tyr Leu Lys Val Val Phe Thr Met Gly Leu Ala Val Pro Met Leu Val
            180                 185                 190

Ala Gly Leu Gly Trp Gly Asp Trp Leu Gly Gly Phe Val Tyr Ala Gly
            195                 200                 205

Ile Leu Arg Ile Phe Phe Val Gln Gln Ala Thr Phe Cys Val Asn Ser
        210                 215                 220

Leu Ala Leu Trp Leu Gly Asp Gln Pro Phe Asp Asp Arg Asn Ser Pro
225                 230                 235                 240

Arg Asp His Val Ile Thr Ala Leu Val Thr Leu Gly Glu Gly Tyr His
                245                 250                 255

Asn Phe His His Glu Phe Pro Ser Asp Tyr Arg Asn Ala Ile Glu Trp
            260                 265                 270

His Gln Tyr Asp Pro Thr Lys Trp Ser Ile Trp Ala Trp Lys Gln Leu
        275                 280                 285

Gly Leu Ala Tyr Asp Leu Lys Lys Phe Arg Ala Asn Glu Ile Glu Lys
        290                 295                 300

Gly Arg Val Gln Gln Leu Gln Lys Lys Leu Asp Arg Lys Arg Ala Thr
305                 310                 315                 320

Leu Asp Trp Gly Thr Pro Leu Asp Gln Leu Pro Val Met Glu Trp Asp
                325                 330                 335

Asp Tyr Val Glu Gln Ala Lys Asn Gly Arg Gly Leu Val Ala Ile Ala
            340                 345                 350

Gly Val Val His Asp Val Thr Asp Phe Ile Lys Asp His Pro Gly Gly
            355                 360                 365

Lys Ala Met Ile Ser Ser Gly Ile Gly Lys Asp Ala Thr Ala Met Phe
        370                 375                 380

Asn Gly Gly Val Tyr Tyr His Ser Asn Ala Ala His Asn Leu Leu Ser
385                 390                 395                 400

Thr Met Arg Val Gly Val Ile Arg Gly Gly Cys Glu Val Glu Ile Trp
                405                 410                 415

Lys Arg Ala Gln Lys Glu Asn Val Glu Tyr Val Arg Asp Gly Ser Gly
            420                 425                 430

Gln Arg Val Ile Arg Ala Gly Glu Gln Pro Thr Lys Ile Pro Glu Pro
        435                 440                 445

Ile Pro Thr Ala Asp Ala Ala
        450                 455

<210> SEQ ID NO 31
<211> LENGTH: 510
<212> TYPE: PRT
<213> ORGANISM: Saccharomyces cerevisiae

<400> SEQUENCE: 31

Met Pro Thr Ser Gly Thr Thr Ile Glu Leu Ile Asp Asp Gln Phe Pro
1               5                   10                  15

Lys Asp Asp Ser Ala Ser Ser Gly Ile Val Asp Glu Val Asp Leu Thr
            20                  25                  30

Glu Ala Asn Ile Leu Ala Thr Gly Leu Asn Lys Lys Ala Pro Arg Ile
        35                  40                  45

Val Asn Gly Phe Gly Ser Leu Met Gly Ser Lys Glu Met Val Ser Val
50                  55                  60

-continued

```
Glu Phe Asp Lys Lys Gly Asn Glu Lys Lys Ser Asn Leu Asp Arg Leu
 65                  70                  75                  80

Leu Glu Lys Asp Asn Gln Glu Lys Glu Ala Lys Thr Lys Ile His
             85                  90                  95

Ile Ser Glu Gln Pro Trp Thr Leu Asn Asn Trp His Gln His Leu Asn
            100                 105                 110

Trp Leu Asn Met Val Leu Val Cys Gly Met Pro Met Ile Gly Trp Tyr
            115                 120                 125

Phe Ala Leu Ser Gly Lys Val Pro Leu His Leu Asn Val Phe Leu Phe
            130                 135                 140

Ser Val Phe Tyr Tyr Ala Val Gly Gly Val Ser Ile Thr Ala Gly Tyr
145                 150                 155                 160

His Arg Leu Trp Ser His Arg Ser Tyr Ser Ala His Trp Pro Leu Arg
                165                 170                 175

Leu Phe Tyr Ala Ile Phe Gly Cys Ala Ser Val Glu Gly Ser Ala Lys
            180                 185                 190

Trp Trp Gly His Ser His Arg Ile His His Arg Tyr Thr Asp Thr Leu
            195                 200                 205

Arg Asp Pro Tyr Asp Ala Arg Arg Gly Leu Trp Tyr Ser His Met Gly
210                 215                 220

Trp Met Leu Leu Lys Pro Asn Pro Lys Tyr Lys Ala Arg Ala Asp Ile
225                 230                 235                 240

Thr Asp Met Thr Asp Asp Trp Thr Ile Arg Phe Gln His Arg His Tyr
                245                 250                 255

Ile Leu Leu Met Leu Leu Thr Ala Phe Val Ile Pro Thr Leu Ile Cys
            260                 265                 270

Gly Tyr Phe Phe Asn Asp Tyr Met Gly Gly Leu Ile Tyr Ala Gly Phe
            275                 280                 285

Ile Arg Val Phe Val Ile Gln Gln Ala Thr Phe Cys Ile Asn Ser Met
            290                 295                 300

Ala His Tyr Ile Gly Thr Gln Pro Phe Asp Asp Arg Arg Thr Pro Arg
305                 310                 315                 320

Asp Asn Trp Ile Thr Ala Ile Val Thr Phe Gly Glu Gly Tyr His Asn
                325                 330                 335

Phe His His Glu Phe Pro Thr Asp Tyr Arg Asn Ala Ile Lys Trp Tyr
            340                 345                 350

Gln Tyr Asp Pro Thr Lys Val Ile Ile Tyr Leu Thr Ser Leu Val Gly
            355                 360                 365

Leu Ala Tyr Asp Leu Lys Lys Phe Ser Gln Asn Ala Ile Glu Glu Ala
            370                 375                 380

Leu Ile Gln Gln Glu Gln Lys Lys Ile Asn Lys Lys Ala Lys Ile
385                 390                 395                 400

Asn Trp Gly Pro Val Leu Thr Asp Leu Pro Met Trp Asp Lys Gln Thr
                405                 410                 415

Phe Leu Ala Lys Ser Lys Glu Asn Lys Gly Leu Val Ile Ile Ser Gly
            420                 425                 430

Ile Val His Asp Val Ser Gly Tyr Ile Ser Glu His Pro Gly Gly Glu
            435                 440                 445

Thr Leu Ile Lys Thr Ala Leu Gly Lys Asp Ala Thr Lys Ala Phe Ser
450                 455                 460

Gly Gly Val Tyr Arg His Ser Asn Ala Ala Gln Asn Val Leu Ala Asp
465                 470                 475                 480
```

```
Met Arg Val Ala Val Ile Lys Glu Ser Lys Asn Ser Ala Ile Arg Met
                485                 490                 495

Ala Ser Lys Arg Gly Glu Ile Tyr Glu Thr Gly Lys Phe Phe
            500                 505                 510

<210> SEQ ID NO 32
<211> LENGTH: 68
<212> TYPE: PRT
<213> ORGANISM: Artificial Sequence
<220> FEATURE:
<223> OTHER INFORMATION: N-terminal residues 1-68 of AnD9DS

<400> SEQUENCE: 32

Met Ser Ala Pro Thr Ala Asp Ile Arg Ala Arg Ala Pro Glu Ala Lys
1               5                   10                  15

Lys Val His Ile Ala Asp Thr Ala Ile Asn Arg His Asn Trp Tyr Lys
            20                  25                  30

His Val Asn Trp Leu Asn Val Phe Leu Ile Ile Gly Ile Pro Leu Tyr
        35                  40                  45

Gly Cys Ile Gln Ala Phe Trp Val Pro Leu Gln Leu Lys Thr Ala Ile
50                  55                  60

Trp Ala Val Ile
65

<210> SEQ ID NO 33
<211> LENGTH: 175
<212> TYPE: PRT
<213> ORGANISM: Artificial Sequence
<220> FEATURE:
<223> OTHER INFORMATION: C-terminal residues 281-455 of AnD9DS

<400> SEQUENCE: 33

Ser Ile Trp Ala Trp Lys Gln Leu Gly Leu Ala Tyr Asp Leu Lys Lys
1               5                   10                  15

Phe Arg Ala Asn Glu Ile Glu Lys Gly Arg Val Gln Gln Leu Gln Lys
            20                  25                  30

Lys Leu Asp Arg Lys Arg Ala Thr Leu Asp Trp Gly Thr Pro Leu Asp
        35                  40                  45

Gln Leu Pro Val Met Glu Trp Asp Asp Tyr Val Glu Gln Ala Lys Asn
50                  55                  60

Gly Arg Gly Leu Val Ala Ile Ala Gly Val Val His Asp Val Thr Asp
65                  70                  75                  80

Phe Ile Lys Asp His Pro Gly Gly Lys Ala Met Ile Ser Ser Gly Ile
            85                  90                  95

Gly Lys Asp Ala Thr Ala Met Phe Asn Gly Gly Val Tyr Tyr His Ser
        100                 105                 110

Asn Ala Ala His Asn Leu Leu Ser Thr Met Arg Val Gly Val Ile Arg
    115                 120                 125

Gly Gly Cys Glu Val Glu Ile Trp Lys Arg Ala Gln Lys Glu Asn Val
130                 135                 140

Glu Tyr Val Arg Asp Gly Ser Gly Gln Arg Val Ile Arg Ala Gly Glu
145                 150                 155                 160

Gln Pro Thr Lys Ile Pro Glu Pro Ile Pro Thr Ala Asp Ala Ala
            165                 170                 175
```

GENERATION OF TRANSGENIC CANOLA WITH LOW OR NO SATURATED FATTY ACIDS

CROSS-REFERENCE TO RELATED APPLICATIONS

This application is a continuation-in-part of application U.S. patent application Ser. No. 13/168,742, filed Jun. 24, 2011, which is a continuation-in-part of application U.S. patent application Ser. No. 11/576,750, which is a national phase entry of PCT International Patent Application No. PCT/US05/36052, filed Oct. 7, 2005, designating the United States of America, and published, in English, as PCT International Publication No. WO 2006/042049 A2 on Apr. 20, 2006. PCT International Patent Application No. PCT/US05/36052 is a continuation of U.S. Provisional Patent Application No. 60/617,532, filed Oct. 8, 2004. The contents of the entirety of each of the foregoing are hereby incorporated in their entireties herein by this reference.

FIELD OF THE INVENTION

Some embodiments generally relate to certain delta-9 desaturase enzymes, nucleic acids encoding these enzymes, and methods of expressing the same in a plant cell. Some embodiments relate to utilizing the activity of certain delta-9 desaturase enzymes to decrease the percent composition of saturated fatty acids in plant materials (e.g., seed) and increasing the percent composition of ω-7 fatty acids. Further embodiments relate to utilizing seed-specific promoters to preferentially express delta-9 desaturase enzymes in seeds. Also disclosed herein are plants and plant materials produced by methods in particular embodiments, and oil produced by those plants which contains less than 3.5% or less than 2.7% saturated fatty acids.

BACKGROUND

Vegetable-derived oils have gradually replaced animal-derived oils and fats as the major source of dietary fat intake. However, saturated fat intake in most industrialized nations has remained at about 15% to 20% of total caloric consumption. In efforts to promote healthier lifestyles, the United States Department of Agriculture (USDA) has recently recommended that saturated fats make up less than 10% of daily caloric intake. To facilitate consumer awareness, current labeling guidelines issued by the USDA now require total saturated fatty acid levels be less than 1.0 g per 14 g serving to receive the "low-sat" label and less than 0.5 g per 14 g serving to receive the "no-sat" label. This means that the saturated fatty acid content of plant oils needs to be less than 7% and 3.5% to receive the "low-sat" or "no-sat" label, respectively. Since issuance of these guidelines, there has been a surge in consumer demand for "low-sat" and "no-sat" oils. To date, this demand has been met principally with canola oil, and to a much lesser degree with sunflower and safflower oils.

While unsaturated fats (monounsaturated and polyunsaturated) are beneficial (especially when consumed in moderation), saturated and trans fats are not. Saturated fat and trans fat raise undesirable LDL cholesterol levels in the blood. Dietary cholesterol also raises LDL cholesterol and may contribute to heart disease even without raising LDL. Therefore, it is advisable to choose foods low in saturated fat, trans fat, and cholesterol as part of a healthful diet.

The characteristics of oils, whether of plant or animal origin, are determined predominately by the number of carbon and hydrogen atoms in the oil molecule, as well as the number and position of double bonds comprised in the fatty acid chain. Most oils derived from plants are composed of varying amounts of palmitic (16:0), stearic (18:0), oleic (18:1), linoleic (18:2) and linolenic (18:3) fatty acids. Conventionally, palmitic and stearic acids are designated as "saturated," because their carbon chains are saturated with hydrogen atoms, and hence have no double bonds; they contain the maximal number of hydrogen atoms possible. However, oleic, linoleic, and linolenic acids are 18-carbon fatty acid chains having one, two, and three double bonds, respectively, therein. Oleic acid is typically considered a monounsaturated fatty acid, whereas linoleic and linolenic are considered to be polyunsaturated fatty acids. The U.S.D.A. definition of "no sat" oil products, meaning those having less than 3.5% saturated fatty acid content, is calculated as the combined saturated fatty acid content by weight (as compared to the total amount of fatty acids).

Canola oil has the lowest level of saturated fatty acids of all vegetable oils. "Canola" refers to rapeseed (*Brassica*) which has an erucic acid (C22:1) content of at most 2% by weight, based on the total fatty acid content of a seed (preferably at most 0.5% by weight, and most preferably essentially 0% by weight), and which produces, after crushing, an air-dried meal containing less than 30 µmol/g of glucosinolates in defatted (oil-free) meal. These types of rapeseed are distinguished by their edibility in comparison to more traditional varieties of the species.

It is postulated that, in oilseeds, fatty acid synthesis occurs primarily in the plastid. The major product of fatty acid synthesis is palmitate (16:0), which appears to be efficiently elongated to stearate (18:0). While still in the plastid, the saturated fatty acids may then be desaturated by an enzyme known as acyl-ACP delta-9 desaturase, to introduce one or more carbon-carbon double bonds. Specifically, stearate may be rapidly desaturated by a plastidial delta-9 desaturase enzyme to yield oleate (18:1). In fact, palmitate may also be desaturated to palmitoleate (16:1) by the plastidial delta-9 desaturase, but this fatty acid appears in only trace quantities (0-0.2%) in most vegetable oils. Thus, the major products of fatty acid synthesis in the plastid are palmitate, stearate, and oleate. In most oils, oleate is the major fatty acid synthesized, as the saturated fatty acids are present in much lower proportions.

Newly-synthesized fatty acids are exported from the plastid to the cytoplasm. Subsequent desaturation of plant fatty acids in the cytoplasm appears to be limited to oleate, which may be desaturated to linoleate (18:2) and linolenate (18:3) by microsomal desaturases acting on oleoyl or linoleoyl substrates esterified to phosphatidyl choline (PC). In addition, depending on the plant, oleate may be further modified by elongation (to 20:1, 22:1, and/or 24:1), or by the addition of functional groups. These fatty acids, along with the saturated fatty acids, palmitate and stearate, are then assembled into triglycerides in endoreticular membranes.

The plant acyl-ACP delta-9 desaturase enzyme is soluble. It is located in the plastid stroma, and uses newly-synthesized fatty acids esterified to ACP, predominantly stearyl-ACP, as substrates. This is in contrast to the other delta-9 desaturase enzymes, which are located in the endoplasmic reticular membrane (ER, or microsomal), use fatty acids esterified to Co-A as substrates, and desaturate both the saturated fatty acids, palmitate and stearate. U.S. Pat. Nos. 5,723,595 and 6,706,950 relate to a plant desaturase.

The yeast delta-9 desaturase gene has been isolated from *Saccharomyces Cerevisiae*, cloned, and sequenced. Stukey et al. (1989) *J. Biol. Chem.* 264:16537-44; Stukey et al. (1990) *J. Biol. Chem.* 265:20144-9. This yeast gene has been introduced into tobacco leaf tissue (Polashcok et al. (1991) *FASEB J.* 5:A1157; Polashok et al. (1992) *Plant Physiol.* 100:894-901), and was apparently expressed in this tissue. Further, this yeast gene was expressed in tomato. See Wang et al. (1996) *J. Agric. Food Chem.* 44:3399-402; and Wang et al. (2001) *Phytochemistry* 58:227-32. While some increases in certain unsaturated fatty acids, and some decreases in certain saturated fatty acids, were reported for both tobacco and tomato using this yeast delta-9 desaturase gene, tobacco and tomato are clearly not oil crops. This yeast gene was also introduced into *Brassica napus*. U.S. Pat. No. 5,777,201.

A different fungal acyl-CoA delta-9 desaturase from *Aspergillus nidulans* has been introduced into canola, thereby achieving reduced saturated fatty acid levels in seed oil. U.S. Patent Application Publication US 2008/0260933 A1. The *A. nidulans* acyl-CoA delta-9 desaturase provided greater depletion of stearate (61-90%) than the more abundant palmitate fatty acids (36-49%) in the seed oil.

BRIEF SUMMARY OF THE INVENTION

Disclosed herein are novel fungal delta-9 desaturase enzymes; nucleic acids comprising at least one nucleotide sequence encoding such a desaturase; and plants, plant materials (e.g., seed), plant parts, and plant commodity products comprising either of the foregoing. Aspects of some embodiments are exemplified by fungal delta-9 desaturase enzymes isolated from *Magnaporthe grisea*, *Leptosphaeria nodorum*, and *Helicoverpa zea*. Some examples include native and synthetic delta-9 desaturases that have a substrate preference for palmitic acid or stearic acid.

Some embodiments comprise an isolated nucleic acid molecule encoding a delta-9 desaturase enzyme comprising an amino acid sequence being at least 80% identical to a sequence selected from the group consisting of SEQ ID NO:1, SEQ ID NO:26, SEQ ID NO:27, SEQ ID NO:28 SEQ ID NO:29, SEQ ID NO:30, SEQ ID NO:31, SEQ ID NO:32, and SEQ ID NO:33. In particular examples, the nucleic acid molecule comprises a sequence being at least 60% identical to a sequence selected from the group consisting of SEQ ID NO:2, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, and SEQ ID NO:25. These and further embodiments may include an isolated delta-9 desaturase polypeptide comprising an amino acid sequence being at least 80% identical to a sequence selected from the group consisting of SEQ ID NO:1, SEQ ID NO:26, SEQ ID NO:27, SEQ ID NO:28 SEQ ID NO:29, SEQ ID NO:30, SEQ ID NO:31, SEQ ID NO:32, and SEQ ID NO:33.

Also disclosed are methods of expressing at least one of the aforementioned nucleic acids and/or polypeptides in a plant cell. Particular embodiments take advantage of a delta-9 desaturase enzyme's activity, such that the percent composition of saturated fatty acids may be decreased in a plant, plant material (e.g., seed), and/or plant part comprising the plant cell, and/or a plant commodity product produced from any of the foregoing. In certain embodiments, ω-7 fatty acids may concomitantly be increased in the plant, plant material, plant part, and/or plant commodity product. Further embodiments take advantage of seed-specific expression to further lower the level of saturated fatty acids in seed oil.

Some embodiments include a method for decreasing the amount of saturated fatty acids in a plant, plant material, plant part, and/or plant commodity product, the method comprising transforming a plant cell with a nucleic acid molecule encoding a delta-9 desaturase polypeptide of the invention, such that the amount of saturated fatty acids in the cell is decreased. Some embodiments include a method for creating a genetically engineered plant that comprises decreased amounts of saturated fatty acids in the plant compared to a wild-type plant of the same species. Such a method may comprise transforming a plant material (or plant cell) with a nucleic acid molecule encoding one or more delta-9 desaturase polypeptides, or one or more copies of a delta-9 desaturase polypeptide of the invention, and culturing the transformed plant material (or plant cell) to obtain a plant. In particular examples, a plant cell and/or plant material from an *Arabidopsis* sp. may be transformed with a nucleic acid molecule encoding a delta-9 desaturase polypeptide of the invention. In other particular examples, the two or more copies of the delta-9 desaturase gene may be transformed, where each delta-9 desaturase gene is controlled by a different promoter. In other particular examples, the two or more promoters are seed specific promoters.

The foregoing and other features will become more apparent from the following detailed description of several embodiments, which proceeds with reference to the accompanying figures.

SEQUENCE LISTING

Figure 1:
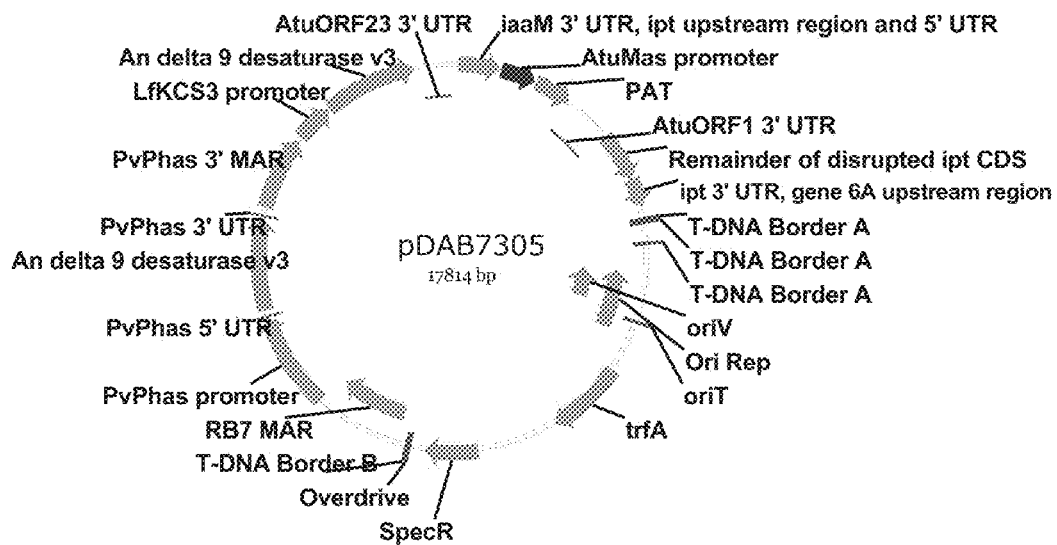
FIG. 1 shows a plasmid map of pDAB7305.

The nucleic acid sequences listed in the accompanying sequence listing are shown using standard letter abbreviations for nucleotide bases, as defined in 37 C.F.R. §1.822. Only one strand of each nucleic acid sequence is shown, but the complementary strand is understood to be included by any reference to the displayed strand. In the accompanying sequence listing:

SEQ ID NO:1 shows the amino acid sequence of *Aspergillus nidulans* acyl-CoA delta-9 desaturase protein (referred to in some places as AnD9DS).

SEQ ID NO:2 shows the nucleic acid sequence of the v3 of the *Aspergillus nidulas* acyl-CoA delta-9 desaturase gene (referred to in some places as AnD9DS).

SEQ ID NO:3 shows the nucleic acid sequence the first plant transcription unit (PTU) of pDAB7305.

SEQ ID NO:4 shows the nucleic acid sequence of the second PTU of pDAB7305.

SEQ ID NO:5 shows the nucleic acid sequence of the third PTU of pDAB7305.

SEQ ID NOS:6-11 show the sequence of primers and probes that may be useful in some embodiments.

SEQ ID NO:12 is an exemplary fragment of a *M. grisea* acyl-CoA delta-9 desaturase gene (referred to in some places as MgD9DS) that was amplified by PCR SEQ ID NO:13 is an exemplary intronless MgD9DS clone SEQ ID NO:14 shows an exemplary nucleic acid sequence encoding a first *Leptosphaeria nodorum* acyl-CoA delta-9 desaturase, referred to in some places as LnD9DS-1

SEQ ID NO:15 shows an exemplary nucleic acid sequence encoding a second exemplary *L. nodorum* acyl-CoA delta-9 desaturase, referred to in some places as LnD9DS-2

SEQ ID NO:16 shows a coding region from an exemplary native delta-9 desaturase gene from *M. grisea* (labeled as MgD9DS v1).

SEQ ID NO:17 shows a coding region from an exemplary native delta-9 desaturase gene from *Helicoverpa zea* (labeled as HzD9DS v/).

SEQ ID NO:18 shows a coding region from an exemplary native delta-9 desaturase (LnD9DS-2 v1) gene from *L. nodorum*.

SEQ ID NO:19 shows the sequence of an exemplary canola-optimized delta-9 desaturase gene from *M. grisea* (MgD9DS v2).

SEQ ID NO:20 shows the sequence of an exemplary canola-optimized delta-9 desaturase gene from *H. zea* (HzD9DS v2).

SEQ ID NO:21 shows the sequence of an exemplary canola-optimized delta-9 desaturase gene from *L. nodorum* (LnD9DS-2 v2).

SEQ ID NO:22 shows the sequence of a further exemplary canola-optimized delta-9 desaturase gene from *L. nodorum* (LnD9DS-2 v3).

SEQ ID NO:23 shows the sequence of a further exemplary canola-optimized delta-9 desaturase gene from *H. zea* (HzD9DS v3).

SEQ ID NO:24 shows an exemplary nucleic acid sequence encoding an *Aspergillus nidulans* delta-9 desaturase, referred to in some places as AnD9DS v2.

SEQ ID NO:25 shows a second exemplary nucleic acid sequence encoding an *A. nidulans* delta-9 desaturase, referred to in some places as AnD9DS v3.

SEQ ID NO:26 shows the amino acid sequence of an exemplary native delta-9 desaturase from *M. grisea* (MgD9DS).

SEQ ID NO:27 shows the amino acid sequence of an exemplary native delta-9 desaturase from *H. zea* (HzD9DS).

SEQ ID NO:28 shows the amino acid sequence of an exemplary native delta-9 desaturase from *L. nodorum* (LnD9DS-2).

SEQ ID NO:29 shows the amino acid sequence encoded by nucleic acids as exemplified by SEQ ID NOs:24-25 (AnD9DS).

SEQ ID NO:30 shows the amino acid sequence of another exemplary AnD9DS desaturase.

SEQ ID NO:31 shows the amino acid sequence of an exemplary native delta-9 desaturase (ScOLE1) from *Saccharomyces cerevisiae*.

SEQ ID NO:32 shows the N-terminal 68 residues (1-68) of an exemplary AnD9DS desaturase.

SEQ ID NO:33 shows the C-terminal 175 residues (281-455) of an exemplary AnD9DS desaturase.

DETAILED DESCRIPTION

I. Overview of Several Embodiments

We previously introduced a fungal acyl-CoA delta-9 desaturase from *Aspergillus nidulans* into canola, thereby achieving reduced saturated fatty acid levels in seed oil. U.S. Patent Application Publication US 2008/0260933 A1. The *A. nidulans* delta-9 desaturase provided greater depletion of stearate (61-90%) than the more abundant palmitate fatty acids (36-49%) in the seed oil. It was discovered that providing multiple copies of the *A. nidulans* delta-9 desaturase was able to reduce the saturated fatty acid levels in canola below 3.5%.

Disclosed herein are nucleic acid molecules encoding a delta-9 desaturase polypeptide comprising a nucleotide sequence being at least 60% identical to a sequence selected from the group consisting of SEQ ID NO:2, SEQ ID NO:3, SEQ ID NO:4, SEQ ID NO:5, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, and SEQ ID NO:25. In some embodiments, the nucleic acid molecule may further comprise a gene regulatory element operably linked to the delta-9 desaturase polypeptide-encoding sequence. In particular embodiments, a gene regulatory element may be a phaseolin promoter, a phaseolin 5' untranslated region, a phaseolin 3' untranslated region ("UTR"), an *Agrobacterium tumefaciens* ORF1 3' untranslated region, a Cassava vein Mosaic Virus promoter, a *Nicotiana tabacum* RB7 Matrix Attachment Region, a T-strand border sequence, a LfKCS3 promoter, and FAE 1 promoter.

In some embodiments, there may be several copies of the nucleic acid molecules encoding a delta-9 desaturase polypeptide, and each may be under the regulatory control of a different set of regulatory elements. More specifically, the gene regulatory elements may be phaseolin promoter and phaseolin 5' UTR, and *Lesquerella fenderi* LfKCS3 promoter, such that two copies of the AND9DS is present, one copy controlled by the phaseolin promoter and 5'UTR, and a second copy controlled by the LfKCS3 promoter. In other embodiments, the several copies of the nucleic acid encoding a delta-9 desaturase polypeptide (or multiple delta-9 destaurase polypeptides) may be under the control of other regulatory elements, including the *Saccharomyces cerevisiae* delta-9 desaturase promoter, the delta-9 desaturase 3'UTR/terminator, the oleI gene promoter, the *Phaseolus vulgaris* phaseolin 3' untranslated region, the *Phaseolus vulgaris* phaseolin matrix attachment region, the *Agrobacterium tumefaciens* Mannopine Synthase promoter, the *Agrobacterium tumefaciens* ORF23 3' untranslated region, the Cassava vein Mosaic Virus Promoter, the *Agrobacterium tumefaciens* ORF1 3' untranslated region, the *Nicotiana tabacum* RB7 Matrix Attachment Region, Overdrive, T-stand border sequences, the LfKCS3 promoter, FAE 1 promoter, a Myc tag, and a hemagglutin tag.

Also disclosed are delta-9 desaturase polypeptides comprising an amino acid sequence being at least 80% identical to a sequence selected from the group consisting of SEQ ID NO:1 as well as nucleic acid molecules encoding such delta-9 desaturase polypeptides, such as SEQ ID NO:2.

In some embodiments, nucleic acid molecules and delta-9 desaturase polypeptides may be expressed in a plant material, cell, tissue, or whole plant, to decrease the amount of saturated fatty acids in the plant material, cells, tissues, or whole plants, relative to the amount observed in a wild-type plant of the same species. Alternative embodiments of the invention include methods for decreasing the amount of saturated fatty acids in the plant material, cell, tissue, or whole plant. Such methods may comprise transforming a plant material, cell, tissue, or whole plant with at least one of the aforementioned nucleic acid molecules, such that the amount of saturated fatty acids in the plant material, cell, tissue, or whole plant is decreased. Particular embodiments include methods for preferentially decreasing palmitic and/or stearic fatty acids in a plant material, cell, tissue, or whole plant.

Methods disclosed herein may be performed, for example, on plants, or plant materials derived from plants (e.g., plants of the genus *Arabidopsis*, or canola). A particular embodiment is drawn to methods for creating or regenerating a genetically engineered plant comprising decreased amounts of saturated fatty acids in the plant compared to a wild-type plant of the same species, the method comprising transforming a plant cell or material with at least one of the aforementioned nucleic acid molecules; and culturing the transformed plant material to obtain a plant. Plants, plant materials, plant cells, and seeds obtained by any of the aforementioned methods are also disclosed.

II. Abbreviations x:yΔ$^z$ fatty acid containing x carbons and y double bonds in position z counting from the carboxyl end
ACP acyl carrier protein
CoA coenzyme A
FA fatty acids
FAS fatty acid synthase
FAME fatty acid methyl ester
KASII β-ketoacyl-ACP synthase II
MUFA monounsaturated fatty acid
PUFA polyunsaturated fatty acid
WT wild type III. Terms Fatty acid: As used herein, the term "fatty acid" refers to long chain aliphatic acids (alkanoic acids) of varying chain lengths, for example, from about C12 to C22, although both longer and shorter chain-length acids are known. The structure of a fatty acid is represented by the notation, x:yΔ$^z$, where "x" is the total number of carbon (C) atoms in the particular fatty acid, and "y" is the number of double bonds in the carbon chain in the position "z," as counted from the carboxyl end of the acid.

Metabolic pathway: The term, "metabolic pathway," refers to a series of chemical reactions occurring within a cell, catalyzed by enzymes, to achieve either the formation of a metabolic product, or the initiation of another metabolic pathway. A metabolic pathway may involve several or many steps, and may compete with a different metabolic pathway for specific reaction substrates. Similarly, the product of one metabolic pathway may be a substrate for yet another metabolic pathway.

Metabolic engineering: For the purposes of the present invention, "metabolic engineering" refers to the rational design of strategies to alter one or more metabolic pathways in a cell, such that the step-by-step modification of an initial substance into a product having the exact chemical structure desired is achieved within the overall scheme of the total metabolic pathways operative in the cell.

Desaturase: As used herein, the term "desaturase" refers to a polypeptide that can desaturate (i.e., introduce a double bond) in one or more fatty acids to produce a fatty acid or precursor of interest. A plant-soluble fatty acid desaturase enzyme may introduce a double bond regiospecifically into a saturated acyl-ACP substrate. Acyl-CoA desaturases introduce a double bond regiospecifically into a saturated fatty acyl-CoA substrate. The reaction involves activation of molecular oxygen by a two-electron reduced diiron center coordinated by a four-helix bundle that forms the core of the desaturase architecture. Of particular interest in some embodiments are acyl-CoA delta-9 desaturases.

The delta-9-18:0$^1$-ACP desaturase is required by all plants for the maintenance of membrane fluidity. While this enzyme primarily desaturates stearoyl-ACP, it is also active to a minor extent with palmitoyl-ACP.

Progeny plant: For the purposes of the present invention, "progeny plant," refers to any plant, or plant material obtained therefrom, that may be obtained by plant breeding methods. Plant breeding methods are well-known in the art, and include natural breeding, artificial breeding, selective breeding involving DNA molecular marker analysis, transgenics, and commercial breeding.

Plant material: As used herein, the term "plant material" refers to any cell or tissue obtained from a plant.

Nucleic acid molecule: A polymeric form of nucleotides, which can include both sense and anti-sense strands of RNA, cDNA, genomic DNA, and synthetic forms and mixed polymers of the above. A nucleotide refers to a ribonucleotide, deoxynucleotide, or a modified form of either type of nucleotide. A "nucleic acid molecule" as used herein is synonymous with "nucleic acid" and "polynucleotide." The term includes single- and double-stranded forms of DNA. A nucleic acid molecule can include either or both naturally occurring and modified nucleotides linked together by naturally occurring and/or non-naturally occurring nucleotide linkages.

Nucleic acid molecules can be modified chemically or biochemically, or can contain non-natural or derivatized nucleotide bases, as will be readily appreciated by those of ordinary skill in the art. Such modification include, for example, labels, methylation, substitution of one or more of the naturally occurring nucleotides with an analog, internucleotide modifications, such as uncharged linkages (for example, methyl phosphonates, phosphotriesters, phosphoramidates, carbamates, etc.), charged linkages (for example, phosphorothioates, phosphorodithioates, etc.), pendent moieties (for example, peptides), intercalators (for example, acridine, psoralen, etc.), chelators, alkylators, and modified linkages (for example, alpha anomeric nucleic acids, etc.). The term "nucleic acid molecule" also includes any topological conformation, including single-stranded, double-stranded, partially duplexed, triplexed, hairpinned, circular and padlocked conformations.

Operably linked: A first nucleic acid sequence is operably linked with a second nucleic acid sequence when the first nucleic acid sequence is in a functional relationship with the second nucleic acid sequence. For instance, a promoter is operably linked to a coding sequence if the promoter affects the transcription or expression of the coding sequence.

When recombinantly produced, operably linked nucleic acid sequences are generally contiguous and, where necessary to join two protein-coding regions, in the same reading frame. However, nucleic acids need not be contiguous to be operably linked Regulatory element: As used herein, the term "regulatory element" refers to a nucleic acid molecule having gene regulatory activity; i.e., one that has the ability to affect the transcription or translation of an operably-linked transcribable nucleic acid molecule. Regulatory elements such as promoters, leaders, introns, and transcription termination regions are non-coding nucleic acid molecules having gene regulatory activity which play an integral part in the overall expression of genes in living cells. Isolated regulatory elements that function in plants are therefore useful for modifying plant phenotypes through the techniques of molecular engineering. By "regulatory element," it is intended a series of nucleotides that determines if, when, and at what level a particular gene is expressed. The regulatory DNA sequences specifically interact with regulatory proteins or other proteins.

As used herein, the term "gene regulatory activity" refers to a nucleic acid molecule capable of affecting transcription or translation of an operably linked nucleic acid molecule. An isolated nucleic acid molecule having gene regulatory activity may provide temporal or spatial expression or modulate levels and rates of expression of the operably linked nucleic acid molecule. An isolated nucleic acid molecule having gene regulatory activity may comprise a promoter, intron, leader, or 3' transcriptional termination region.

Promoters: As used herein, the term "promoter" refers to a nucleic acid molecule that is involved in recognition and binding of RNA polymerase II or other proteins such as transcription factors (trans-acting protein factors that regulate transcription) to initiate transcription of an operably linked gene. Promoters may themselves contain sub-elements such as cis-elements or enhancer domains that effect the transcription of operably linked genes. A "plant promoter" is a native or non-native promoter that is functional in plant cells. A plant promoter can be used as a 5' regulatory element for modulating expression of an operably linked gene or genes. Plant promoters may be defined by their temporal, spatial, or developmental expression pattern. The nucleic acid molecules described herein may comprise nucleic acid sequences comprising promoters.

Sequence identity: The term "sequence identity" or "identity," as used herein in the context of two nucleic acid or polypeptide sequences, may refer to the residues in the two sequences that are the same when aligned for maximum correspondence over a specified comparison window.

When percentage of sequence identity is used in reference to proteins, it is recognized that residue positions which are not identical often differ by conservative amino acid substitutions, where amino acid residues are substituted for other amino acid residues with similar chemical properties (e.g., charge, hydrophobicity, or steric effects), and therefore do not change the functional properties of the molecule.

Therefore, when sequences differ by conservative substitutions, the percent sequence identity may be adjusted upwards to correct for the conservative nature of the substitution at the site of the non-identical residue. Sequences that differ by such conservative substitutions are said to have "sequence similarity" or "similarity." Techniques for making this adjustment are well known to those of ordinary skill in the art. Typically, such techniques involve scoring a conservative substitution as a partial, rather than a full, mismatch, thereby increasing the percentage sequence identity. For example, where an identical amino acid is given a score between 0 and 1, and a non-conservative substitution is given a score of 0, a conservative substitution is given a score between 0 and 1. The scoring of conservative substitutions may be calculated, for example, as implemented in the program PC/GENE (Intelligenetics, Mountain View, Calif.).

As used herein, the term "percentage of sequence identity" may refer to the value determined by comparing two optimally aligned sequences over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleotide or amino acid residue occurs in both sequences to yield the number of matched positions, dividing the number of matched positions by the total number of positions in the comparison window, and multiplying the result by 100 to yield the percentage of sequence identity.

Analogous position in an amino acid sequence: Nucleic acid and amino acid sequences may be aligned by the methods described in the following paragraphs. When aligned, a position in one sequence is in "an analogous position" with a position in the aligned sequence if the positions are identical within the consensus sequence.

Methods for aligning sequences for comparison are well-known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. USA* 85:2444, 1988; Higgins and Sharp, *Gene* 73:237-44, 1988; Higgins and Sharp, *CABIOS* 5:151-3, 1989; Corpet et al., *Nucleic Acids Research* 16:10881-10890, 1988; Huang, et al., *Computer Applications in the Biosciences* 8:155-65, 1992; Pearson et al., *Methods in Molecular Biology* 24:307-31, 1994; Tatiana et al., *FEMS Microbiol. Lett.*, 174:247-50, 1990; Altschul et al., *J. Mol. Biol.* 215:403-10, 1990 (detailed consideration of sequence-alignment methods and homology calculations).

The National Center for Biotechnology Information (NCBI) Basic Local Alignment Search Tool (BLAST) is available on the Internet (at blast.ncbi.nlm.nih.gov/Blast.cgi), for use in connection with sequence-analysis programs, for example, blastp and blastn. A description of how to determine sequence identity using this program is available on the Internet through NCBI at blast.ncbi.nlm.nih.gov/Blast.cgi?CMD=Web&PAGE_TYPE=BlastDocs.

For comparisons of amino acid sequences, the "Blast 2 sequences" function of the BLAST program (bl2seq) is employed using the default parameters. Specific parameters may be adjusted within the discretion of one of skill in the art, to for example, provide a penalty for a mismatch or reward for a match.

Transformed: As used herein, the term "transformed" refers to a cell, tissue, organ, or organism into which has been introduced a foreign nucleic acid molecule, such as a construct. The introduced nucleic acid molecule may be integrated into the genomic DNA of the recipient cell, tissue, organ, or organism such that the introduced polynucleotide molecule is inherited by subsequent progeny. A "transgenic" or "transformed" cell or organism also includes progeny of the cell or organism and progeny produced from a breeding program employing such a transgenic plant as a parent in,

IV. Metabolic Engineering Approaches to Decreasing Saturated Fatty Acids in a Host Cell, Tissue, or Organism

A. Overview

An embodiment of the invention includes introducing delta-9 desaturases with specific acyl-CoA preferences (for example, for palmitic or stearic acid) in plant seeds. The specific acyl-CoA preference of the delta-9 desaturase enables targeting of certain specific saturated fatty acid pools (e.g., palmitate for conversion to monounsaturated products). Acyl-CoA delta-9 desaturases were selected for lowering the saturated fatty acid content in plants as they are not normally produced in plant systems to any appreciable extent.

B. Polypeptides

Polypeptides according to some embodiments of the present invention comprise an amino acid sequence showing increasing percentage identities when aligned with a sequence selected from the group consisting of SEQ ID NO:1, SEQ ID NO:26, SEQ ID NO:27, SEQ ID NO:28 SEQ ID NO:29, SEQ ID NO:30, SEQ ID NO:31, SEQ ID NO:32, and SEQ ID NO:33. Specific amino acid sequences within these and other embodiments may comprise sequences having, for example, at least about 70%, about 75%, about 80%, 81%, 82%, 83%, 84%, 85%, 86%, 87%, 88%, 89%, 90%, 91%, 92%, 93%, 94%, 95% 96%, 97%, 98%, 99%, or 100% identity with the aforementioned sequences. In many embodiments, the amino acid sequence having the aforementioned sequence identity when aligned with the aforementioned sequences encode a peptide with enzymatic delta-9-18:0-ACP desaturase activity, or part of a such a peptide.

C. Nucleic acids

Some embodiments include nucleic acid molecules encoding a polypeptide described above. For example, nucleic acid sequences in some embodiments show increasing percentage identities when aligned with a sequence selected from the group consisting of SEQ ID NO:2, SEQ ID NO:3, SEQ ID NO:4, SEQ ID NO:5, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, and SEQ ID NO:25. Specific nucleic acid sequences within these and other embodiments may comprise sequences having, for example, at least about 60%, about 65%, about 70%, about 75%, about 80%, 81%, 82%, 83%, 84%, 85%, 86%, 87%, 88%, 89%, 90%, 91%, 92%, 93%, 94%, 95% 96%, 97%, 98%, 99%, or 100% identity with a sequence selected from the group consisting of SEQ ID NO:2, SEQ ID NO:3, SEQ ID NO:4, SEQ ID NO:5, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, and SEQ ID NO:25. It is understood by those of ordinary skill in the art that nucleic acid molecules may be modified without substantially changing the amino acid sequence of an encoded polypeptide, for example, by introducing permissible nucleotide substitutions according to codon degeneracy.

In some embodiments, nucleic acid molecules of the present invention comprise a gene regulatory element (e.g., a promoter). Promoters may be selected on the basis of the cell type into which the vector construct will be inserted. Promoters which function in bacteria, yeast, and plants are well-known in the art. The promoters may also be selected on the basis of their regulatory features. Examples of such features include enhancement of transcriptional activity, inducibility, tissue-specificity, and developmental stage-specificity. In plants, promoters that are inducible, of viral or synthetic origin, constitutively active, temporally regulated, and spatially regulated have been described. See, e.g., Poszkowski et al. (1989) *EMBO J.* 3:2719; Odell et al. (1985) *Nature* 313:810; and Chau et al. (1989) *Science* 244:174-81).

Useful inducible promoters include, for example, promoters induced by salicylic acid or polyacrylic acids induced by application of safeners (substituted benzenesulfonamide herbicides), heat-shock promoters, a nitrate-inducible promoter derived from the spinach nitrate reductase transcribable nucleic acid molecule sequence, hormone-inducible promoters, and light-inducible promoters associated with the small subunit of RuBP carboxylase and LHCP families.

Examples of useful tissue-specific, developmentally-regulated promoters include the β-conglycinin 7Sα promoter and seed-specific promoters. Plant functional promoters useful for preferential expression in seed plastid include those from proteins involved in fatty acid biosynthesis in oilseeds and from plant storage proteins. Examples of such promoters include the 5' regulatory regions from such transcribable nucleic acid molecule sequences as phaseolin, napin, zein, soybean trypsin inhibitor, ACP, stearoyl-ACP desaturase, and oleosin. Another exemplary tissue-specific promoter is the lectin promoter, which is specific for seed tissue.

More specifically, promoters may include the *Phaseolus vulgaris* Phaseolin promoter, (alone or in conjunction with the *Phaseolus vulgaris* Phaseolin 3' untranslated region and the *Phaseolus vulgaris* Phaseolin 3' Matrix Attachment Region), the *Lesquerella fendleri* KCS3 promoter, or the *Agrobacterium tumefaciens* Mannopine Synthase promoter.

Other useful promoters include the nopaline synthase, mannopine synthase, and octopine synthase promoters, which are carried on tumor-inducing plasmids of *Agrobacterium tumefaciens*; the cauliflower mosaic virus (CaMV) 19S and 35S promoters; the enhanced CaMV 35S promoter; the Figwort Mosaic Virus 35S promoter; the light-inducible promoter from the small subunit of ribulose-1,5-bisphosphate carboxylase (ssRUBISCO); the EIF-4A promoter from tobacco (Mandel et al. (1995) Plant Mol. Biol. 29:995-1004); corn sucrose synthetase; corn alcohol dehydrogenase I; corn light harvesting complex; corn heat shock protein; the chitinase promoter from *Arabidopsis*; the LTP (Lipid Transfer Protein) promoters; petunia chalcone isomerase; bean glycine rich protein 1; potato patatin; the ubiquitin promoter; and the actin promoter. Useful promoters are preferably seed-selective, tissue selective, or inducible. Seed-specific regulation is discussed in, for example, EP 0 255 378.

To obtain higher expression of a heterologous gene(s), it may be preferred to reengineer the gene(s) so that it is more efficiently expressed in the expression host cell (e.g., a plant cell, for example, canola, rice, tobacco, maize, cotton, and soybean). Therefore, an optional additional step in the design of a gene encoding a delta-9 desaturase for plant expression (i.e., in addition to the provision of one or more gene regulatory elements) is reengineering of a heterologous gene protein coding region for optimal expression. Particular embodiments include redesigned genes that have been optimized to increase the expression level (i.e. produce more protein) in a transgenic canola plant cell or *Arabidopsis* plant cell than in a canola plant cell or *Arabidopsis* plant cell transformed with the naturally-occurring heterologous gene sequence.

Due to the plasticity afforded by the redundancy/degeneracy of the genetic code (i.e., some amino acids are specified by more than one codon), evolution of the genomes in different organisms or classes of organisms has resulted in differential usage of synonymous codons. This "codon bias" is reflected in the mean base composition of protein coding regions. For example, organisms having genomes with relatively low G+C contents utilize more codons having A or T in the third position of synonymous codons, whereas those having higher G+C contents utilize more codons having G or C in the third position. Further, it is thought that the presence of "minor" codons within an mRNA may reduce the absolute translation rate of that mRNA, especially when the relative abundance of the charged tRNA corresponding to the minor codon is low. An extension of this reasoning is that the diminution of translation rate by individual minor codons would be at least additive for multiple minor codons. Therefore, mRNAs having high relative contents of minor codons in a particular expression host would have correspondingly low translation rates. This rate may be reflected by correspondingly low levels of the encoded protein.

In engineering optimized genes encoding a delta-9 desaturase for expression in canola or *Arabidopsis* (or other plants, such as rice, tobacco, maize, cotton or soybean), it is helpful if the codon bias of the prospective host plant(s) has been determined. Multiple publicly-available DNA sequence databases exist wherein one may find information about the codon distribution of plant genomes or the protein coding regions of various plant genes.

The codon bias is the statistical distribution of codons that the expression host (e.g., a plant such as canola or *Arabidopsis*) uses for coding the amino acids of its proteins. The codon bias can be calculated as the frequency at which a single codon is used relative to the codons for all amino acids. Alternatively, the codon bias may be calculated as the frequency at which a single codon is used to encode a particular amino acid, relative to all the other codons for that amino acid (synonymous codons).

In designing optimized coding regions for plant expression of delta-9 desaturase genes, the primary ("first choice") codons preferred by the plant should be determined, as well as the second, third, fourth etc. choices of preferred codons when multiple choices exist. A new DNA sequence can then be designed which encodes the amino sequence of the delta-9 desaturase gene, wherein the new DNA sequence differs from the native DNA sequence (encoding the desaturase) by the substitution of expression host-preferred (first preferred, second preferred, third preferred, or fourth preferred, etc.) codons to specify the amino acid at each position within the amino acid sequence. The new sequence is then analyzed for restriction enzyme sites that might have been created by the modifications. The identified putative restriction sites are further modified by replacing these codons with a next-preferred codon to remove the restriction site. Other sites in the sequence which may affect transcription or translation of heterologous sequence are exon:intron junctions (5' or 3'), poly-A addition signals, and/or RNA polymerase termination signals. The sequence may be further analyzed and modified to reduce the frequency of TA or CG doublets. In addition to these doublets, sequence blocks that have more than about six G or C nucleotides that are the same may also adversely affect transcription or translation of the sequence. Therefore, these blocks are advantageously modified by replacing the codons of first or second choice, etc. with the next-preferred codon of choice.

The method described above enables one skilled in the art to modify gene(s) that are foreign to a particular plant so that the genes are optimally expressed in plants. The method is further illustrated in PCT application WO 97/13402. Thus, optimized synthetic genes that are functionally equivalent to desaturases/genes of some embodiments may be used to transform hosts, including plants. Additional guidance regarding the production of synthetic genes can be found in, for example, U.S. Pat. No. 5,380,831.

Once a plant-optimized DNA sequence has been designed on paper or in silico, actual DNA molecules can be synthesized in the laboratory to correspond in sequence precisely to the designed sequence. Such synthetic DNA molecules may be cloned and otherwise manipulated exactly as if they were derived from natural or native sources.

D. Methods for Genetic Transformation of Plant Material

Some embodiments are directed to a method of producing a transformed cell that comprises one or more nucleic acid molecule(s) comprising a nucleic acid sequence at least 60% identical to a sequence selected from the group consisting of SEQ ID NO:2, SEQ ID NO:3, SEQ ID NO:4, SEQ ID NO:5, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, and SEQ ID NO:25. Such nucleic acid molecules may also comprise, for example, non-coding regulatory elements, such as promoters. Other sequences may also be introduced into the cell along with the non-coding regulatory elements and transcribable nucleic acid molecule sequences. These other sequences may include 3' transcriptional terminators, 3' poly-adenylation signals, other untranslated sequences, transit or targeting sequences, selectable markers, enhancers, and operators.

A method of transformation generally comprises the steps of selecting a suitable host cell, transforming the host cell with a recombinant vector, and obtaining the transformed host cell. Technology for introduction of DNA into cells is well-known to those of skill in the art. These methods can generally be classified into five categories: (1) chemical methods (Graham and Van der Eb (1973) *Virology* 54(2): 536-9; Zatloukal et al. (1992) *Ann. N.Y. Acad. Sci.* 660:136-53); (2) physical methods such as microinjection (Capechi (1980) *Cell* 22(2):479-88), electroporation (Wong and Neumann (1982) *Biochim. Biophys. Res. Commun.* 107(2):584-7; Fromm et al. (1985) *Proc. Natl. Acad. Sci. USA* 82(17): 5824-8; U.S. Pat. No. 5,384,253), and particle acceleration (Johnston and Tang (1994) *Methods Cell Biol.* 43(A):353-65; Fynan et al. (1993) *Proc. Natl. Acad. Sci. USA* 90(24): 11478-82; (3) viral vectors (Clapp (1993) *Clin. Perinatol.* 20(1):155-68; Lu et al. (1993) J. Exp. Med. 178(6):2089-96; Eglitis and Anderson (1988) *Biotechniques* 6(7):608-14); (4) receptor-mediated mechanisms (Curiel et al. (1992) *Hum. Gen. Ther.* 3(2):147-54; Wagner et al. (1992) *Proc. Natl. Acad. Sci. USA* 89(13):6099-103); and (5) bacterial-mediated mechanisms, such as with *Agrobacterium*. Alternatively, nucleic acids may be directly introduced into pollen by directly injecting a plant's reproductive organs. Zhou et al. (1983) *Methods in Enzymology* 101:433; Hess (1987) *Intern. Rev. Cytol.* 107:367; Luo et al. (1988) *Plant Mol. Biol. Reporter* 6:165; Pena et al. (1987) *Nature* 325:274. Other transformation methods include, for example, protoplast transformation as illustrated in U.S. Pat. No. 5,508, 184. Nucleic acid molecules may also be injected into immature embryos. Neuhaus et al. (1987) *Theor. Appl. Genet.* 75:30.

The most commonly used methods for transformation of plant cells are: the *Agrobacterium*-mediated DNA transfer process (Fraley et al. (1983) *Proc. Natl. Acad. Sci. USA* 80:4803) (as illustrated in U.S. Pat. No. 5,824,877; U.S. Pat. No. 5,591,616; U.S. Pat. No. 5,981,840; and U.S. Pat. No. 6,384,301) and the biolistics or microprojectile bombardment-mediated process (i.e., the gene gun) (such as described in U.S. Pat. No. 5,550,318; U.S. Pat. No. 5,538, 880; U.S. Pat. No. 6,160,208; U.S. Pat. No. 6,399,861; and U.S. Pat. No. 6,403,865). Typically, nuclear transformation is desired, but where it is desirable to specifically transform plastids, such as chloroplasts or amyloplasts, plant plastids may be transformed utilizing a microprojectile-mediated delivery of the desired nucleic acid molecule in certain plant species, such as for example, *Arabidopsis*, tobacco, potato, and *Brassica* species.

*Agrobacterium*-mediated transformation is achieved through the use of a genetically engineered soil bacterium belonging to the genus *Agrobacterium*. Several *Agrobacterium* species mediate the transfer of a specific DNA known as "T-DNA," which can be genetically engineered to carry any desired piece of DNA into many plant species. The major events marking the process of T-DNA mediated pathogensis are: induction of virulence genes, and processing and transfer of T-DNA. This process is the subject of many reviews. See, e.g., Ream (1989) *Ann. Rev. Phytopathol.* 27:583-618; Howard and Citovsky (1990) *Bioassays* 12:103-8; Kado (1991) *Crit. Rev. Plant Sci.* 10:1-32; Zambryski (1992) *Annual Rev. Plant PhysioL Plant Mol. Biol.* 43:465-90; Gelvin (1993) in *Transgenic Plants*, Kung and Wu eds., Academic Press, San Diego, Calif., pp. 49-87; Binns and Howitz (1994) In *Bacterical Pathogenesis of Plants and Animals*, Dang, ed., Berlin: Springer Verlag., pp. 119-38; Hooykaas and Beijersbergen (1994) *Ann. Rev. Phytopathol.* 32:157-79; Lessl and Lanka (1994) *Cell* 77:321-4; and Zupan and Zambryski (1995) *Annual Rev. Phytopathol.* 27:583-618.

To select or score for transformed plant cells regardless of transformation methodology, the DNA introduced into the cell may contain a gene that functions in a regenerable plant tissue to produce a compound that confers upon the plant tissue resistance to an otherwise toxic compound. Genes of interest for use as a selectable, screenable, or scorable marker include, but are not limited to, β-glucuronidase (GUS), green fluorescent protein (GFP), luciferase, and antibiotic or herbicide tolerance genes. Examples of antibiotic resistance genes include genes conferring resistance to the penicillins, kanamycin (and neomycin, G418, bleomycin); methotrexate (and trimethoprim); chloramphenicol; and tetracycline. For example, glyphosate resistance may be conferred by a herbicide resistance gene. Della-Cioppa et al. (1987) *Bio/Technology* 5:579-84. Other selection devices can also be implemented, including for example and without limitation, tolerance to phosphinothricin, bialaphos, and positive selection mechanisms (Joersbro et al. (1998) *Mol. Breed.* 4:111-7), and are considered within the scope of embodiments of the present invention.

The transformed cells, identified by selection or screening and cultured in an appropriate medium that supports regeneration, may then be allowed to mature into plants.

The presently disclosed methods may be used with any transformable plant cell or tissue. Transformable cells and tissues, as used herein, includes but is not limited to those cells or tissues that are capable of further propagation to give rise to a plant. Those of skill in the art recognize that a number of plant cells or tissues are transformable in which after insertion of exogenous DNA and appropriate culture conditions the plant cells or tissues can form into a differentiated plant. Tissue suitable for these purposes can include but is not limited to immature embryos, scutellar tissue, suspension cell cultures, immature inflorescence, shoot meristem, nodal explants, callus tissue, hypocotyl tissue, cotyledons, roots, and leaves.

The regeneration, development, and cultivation of plants from transformed plant protoplast or explants are known in the art. Weissbach and Weissbach (1988) *Methods for Plant Molecular Biology*, (Eds.) Academic Press, Inc., San Diego, Calif.; Horsch et al. (1985) *Science* 227:1229-31. This regeneration and growth process typically includes the steps of selecting transformed cells and culturing those cells through the usual stages of embryonic development through the rooted plantlet stage. Transgenic embryos and seeds are similarly regenerated. In this method, transformants are generally cultured in the presence of a selective media which selects for the successfully transformed cells and induces the regeneration of plant shoots. Fraley et al. (1993) *Proc. Natl. Acad. Sci. USA* 80:4803. These shoots are typically obtained within two to four months. The resulting transgenic rooted shoots are thereafter planted in an appropriate plant growth medium such as soil. Cells that survive the exposure to a selective agent, or cells that have been scored positive in a screening assay, may be cultured in media that supports regeneration of plants. The shoots may then be transferred to an appropriate root-inducing medium containing the selective agent and an antibiotic to prevent bacterial growth. Many of the shoots will develop roots. These are then transplanted to soil or other media to allow the continued development of roots. The method, as outlined above, will generally vary depending on the particular plant strain employed, and particulars of the methodology are therefore within the discretion of one of skill in the art.

The regenerated transgenic plants may be self-pollinated to provide homozygous transgenic plants. Alternatively, pollen obtained from the regenerated transgenic plants may be crossed with non-transgenic plants, preferably inbred lines of agronomically important species. Conversely, pollen from non-transgenic plants may be used to pollinate the regenerated transgenic plants.

The transgenic plant may pass along the transformed nucleic acid sequence to its progeny. The transgenic plant is preferably homozygous for the transformed nucleic acid sequence and transmits that sequence to all of its offspring upon, and as a result of, sexual reproduction. Progeny may be grown from seeds produced by the transgenic plant. These additional plants may then be self-pollinated to generate a true breeding line of plants.

The progeny from these plants may be evaluated, among other things, for gene expression. The gene expression may be detected by several common methods such as western blotting, northern blotting, immunoprecipitation, and ELISA (Enzyme-Linked ImmunoSorbent Assay). The transformed plants may also be analyzed for the presence of the introduced DNA and the expression level and/or fatty acid profile conferred by the nucleic acid molecules and amino acid molecules of the present invention. Those of skill in the art are aware of the numerous methods available for the analysis of transformed plants. For example, methods for plant analysis include, but are not limited to, Southern blots or northern blots, PCR-based approaches, biochemical assays, phenotypic screening methods, field evaluations, and immunodiagnostic assays.

Methods for specifically transforming dicots are well-known to those skilled in the art. Transformation and plant regeneration using these methods have been described for a number of crops including, but not limited to, members of the genus *Arabidopsis*, cotton (*Gossypium hirsutum*), soybean (*Glycine max*), peanut (*Arachis hypogaea*), and members of the genus *Brassica*. Methods for transforming dicots, primarily by use of *Agrobacterium tumefaciens*, and obtaining transgenic plants have been published for cotton (U.S. Pat. No. 5,004,863; U.S. Pat. No. 5,159,135; U.S. Pat. No. 5,518,908); soybean (U.S. Pat. No. 5,569,834; U.S. Pat. No. 5,416,011; McCabe et al. (1988) *Biotechnology* 6:923; Christou et al. (1988) *Plant Physiol.* 87:671-4); *Brassica* (U.S. Pat. No. 5,463,174); peanut (Cheng et al. (1996) *Plant Cell Rep.* 15:653-7; McKently et al. (1995) *Plant Cell Rep.* 14:699-703); papaya; and pea (Grant et al. (1995) *Plant Cell Rep.* 15:254-8).

Methods for transforming monocots are also well-known in the art. Transformation and plant regeneration using these methods have been described for a number of crops including, but not limited to, barley (*Hordeum vulgarae*); maize (*Zea mays*); oats (*Avena sativa*); orchard grass (*Dactylis glomerate*); rice (*Oryza sativa*, including indica and japonica varieties); sorghum (*Sorghum bicolor*); sugar cane (*Saccharum* sp); tall fescue (*Festuca arundinacea*); turfgrass species (e.g., *Agrostis stolonifera*, *Poa pratensis*, *Stenotaphrum secundatum*); wheat (*Triticum aestivum*); and alfalfa (*Medicago sativa*). It is apparent to those of skill in the art that a number of transformation methodologies can be used and modified for production of stable transgenic plants for any number of target crops of interest.

Any plant may be chosen for use in the presently disclosed methods. Preferred plants for modification according to the present invention include, for example and without limitation, oilseed plants, *Arabidopsis thaliana*, borage (*Borago* spp.), canola (*Brassica* spp.), castor (*Ricinus communis*), cocoa bean (*Theobroma cacao*), corn (*Zea mays*), cotton (*Gossypium* spp), Crambe spp., Cuphea spp., flax (*Linum* spp.), *Lesquerella* and *Limnanthes* spp., Linola, nasturtium (*Tropaeolum* spp.), *Oenothera* spp., olive (*Olea* spp.), palm (*Elaeis* spp.), peanut (*Arachis* spp.), rapeseed, safflower (*Carthamus* spp.), soybean (*Glycine* and *Soja* spp.), sunflower (*Helianthus* spp.), tobacco (*Nicotiana* spp.), *Vernonia* spp., wheat (*Triticum* spp.), barley (*Hordeum* spp.), rice (*Oryza* spp.), oat (*Avena* spp.) sorghum (*Sorghum* spp.), and rye (*Secale* spp.) or other members of the *Gramineae*.

It is apparent to those of skill in the art that a number of transformation methodologies can be used and modified for production of stable transgenic plants from any number of target crops of interest.

E. Transgenic Seeds

In some embodiments, a transgenic seed may comprise a delta-9 desaturase polypeptide comprising an amino acid sequence being at least 80% identical to a sequence selected from the group consisting of SEQ ID NO:1, SEQ ID NO:26, SEQ ID NO:27, SEQ ID NO:28 SEQ ID NO:29, SEQ ID NO:30, SEQ ID NO:31, SEQ ID NO:32, and SEQ ID NO:33. In these and other embodiments, the transgenic seed may comprise a nucleic acid sequence being at least 60% identical to a sequence selected from the group consisting of SEQ ID NO:2, SEQ ID NO:3, SEQ ID NO:4, SEQ ID NO:5, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, and SEQ ID NO:25. In certain embodiments, a transgenic seed may exhibit decreased levels of saturated fatty acids (for example, palmitic fatty acids and/or stearic fatty acids). The seeds may be harvested from a fertile transgenic plant, and may be used to grow progeny generations of transformed plants, including hybrid plant lines comprising at least one nucleic acid sequence as set forth above, and optionally at least one additional gene or nucleic acid construct of interest.

Each document, patent, and reference cited herein is herein incorporated by its entirety.

The following examples are provided to illustrate certain particular features and/or embodiments. These examples should not be construed to limit the invention to the particular features or embodiments described.

EXAMPLES

Example 1

Construct Design of pDAB7305

The *Aspergillus nidulans* Δ-9 Desaturase (AnD9DS) enzyme was previously disclosed in U.S. Patent App. No. 2008/0260933, herein incorporated by reference in its entirety, and is presented herein as SEQ ID NO:1. A polynucleotide sequence (SEQ ID NO:2) comprising the AnD9DS v3 coding sequence was synthesized and incorporated into plasmid construct pDAB7305 (FIG. 1) for *Agrobacterium*-mediated plant transformation. The resulting construct contained three plant transcription units (also described and used interchangeably as a gene expression cassette). The first plant transcription unit (PTU) (SEQ ID NO:3) was comprised of the RB7 Matrix Attachment Region (RB7 MAR; International Patent App. No. WO9727207), *Phaseolus vulgaris* Phaseolin promoter (Pv Phas promoter; U.S. Pat. No. 5,504,200), AnD9DS coding sequence (An delta 9 desaturase v3), *Phaseolus vulgaris* Phaseolin 3' untranslated region (Pv Phas 3'UTR; U.S. Pat. No. 5,504,200), and the *Phaseolus vulgaris* Phaseolin 3' Matrix Attachment Region (Pv Phas 3' MAR; U.S. Pat. No. 5,504,200). The second PTU (SEQ ID NO:4) was comprised of the *Lesquerella fendleri* KCS3 promoter (LfKCS3 promoter; U.S. Pat. No. 7,253,337), AnD9DS coding sequence (An delta 9 desaturase v3), and *Agrobacterium tumefaciens* ORF 23 3' untranslated region (AtuORF23 3'UTR; U.S. Pat. No. 5,428,147). The third PTU (SEQ ID NO:5) was comprised of *Agrobacterium tumefaciens* Mannopine Synthase promoter (AtuMas promoter; Barker, R. F., Idler, K. B., Thompson, D. V., Kemp, J. D., (1983), a polynucleotide sequence of the T-DNA region from the *Agrobacterium tumefaciens* octopine Ti plasmid pTi15955, *Plant Molecular Biology*, 2(6), 335-50), phosphinothricin acetyl transferase gene (PAT; Wohlleben et al., (1988) *Gene*, 70: 25-37), and *Agrobacterium tumefaciens* ORF 1 3' untranslated region (AtuORF1 3'UTR; Huang et al., (1990) *J. Bacteriol.*, 172:1814-1822). The construct was confirmed via restriction enzyme digestion and sequencing. Finally, the construct was transformed into *Agrobacterium tumefaciens* and stored as a glycerol stock.

Example 2

*Agrobacterium*-Mediated Transformation of Canola (*Brassica napus*) Hypocotyls *Agrobacterium* Preparation The *Agrobacterium* strain containing the pDAB7305 binary plasmid was streaked out on YEP media (Bacto Peptone™ 20.0 gm/L and Yeast Extract 10.0 gm/L) plates containing streptomycin (100 mg/ml) and spectinomycin (50 mg/mL) and incubated for 2 days at 28° C. The propagated *Agrobacterium* strain containing the pDAB7305 binary plasmid was scraped from the 2-day streak plate using a sterile inoculation loop. The scraped *Agrobacterium* strain containing the pDAB7305 binary plasmid was then inoculated into 150 mL modified YEP liquid with streptomycin (100 mg/ml) and spectinomycin (50 mg/ml) into sterile 500 mL baffled flask(s) and shaken at 200 rpm at 28° C. The cultures were centrifuged and resuspended in M-medium (LS salts, 3% glucose, modified B5 vitamins, 1 µM kinetin, 1 µM 2,4-D, pH 5.8) and diluted to the appropriate density (50 Klett Units as measured using a spectrophotometer) prior to transformation of Canola hypocotyls.

Canola Transformation

Seed Germination:

Canola seeds (var. NEXERA 710™) were surface-sterilized in 10% Clorox™ for 10 minutes and rinsed three times with sterile distilled water (seeds are contained in steel strainers during this process). Seeds were planted for germination on ½ MS Canola medium (½ MS, 2% sucrose, 0.8% agar) contained in Phytatrays™ (25 seeds per Phytatray™) and placed in a Percival™ growth chamber with growth regime set at 25° C., photoperiod of 16 hours light and 8 hours dark for 5 days of germination.

Pre-Treatment:

On day 5, hypocotyl segments of about 3 mm in length were aseptically excised, the remaining root and shoot sections were discarded (drying of hypocotyl segments was prevented by immersing the hypocotyls segments into 10 mL of sterile milliQ™ water during the excision process). Hypocotyl segments were placed horizontally on sterile filter paper on callus induction medium, MSK1D1 (MS, 1 mg/L kinetin, 1 mg/L 2,4-D, 3.0% sucrose, 0.7% phytagar) for 3 days pre-treatment in a Percival™ growth chamber with growth regime set at 22-23° C., and a photoperiod of 16 hours light, 8 hours dark.

Co-Cultivation with *Agrobacterium*:

The day before *Agrobacterium* co-cultivation, flasks of YEP medium containing the appropriate antibiotics, were inoculated with the *Agrobacterium* strain containing the pDAB7305 binary plasmid. Hypocotyl segments were transferred from filter paper callus induction medium, MSK1D1 to an empty 100×25 mm Petri™ dishes containing 10 mL of liquid M-medium to prevent the hypocotyl segments from drying. A spatula was used at this stage to scoop the segments and transfer the segments to new medium. The liquid M-medium was removed with a pipette and 40 mL of *Agrobacterium* suspension was added to the Petri™ dish (500 segments with 40 mL of *Agrobacterium* solution). The hypocotyl segments were treated for 30 minutes with periodic swirling of the Petri™ dish so that the hypocotyl segments remained immersed in the *Agrobacterium* solution. At the end of the treatment period, the *Agrobacterium* solution was pipetted into a waste beaker; autoclaved and discarded (the *Agrobacterium* solution was completely removed to prevent *Agrobacterium* overgrowth). The treated hypocotyls were transferred with forceps back to the original plates containing MSK1D1 media overlaid with filter paper (care was taken to ensure that the segments did not dry). The transformed hypocotyl segments and non-transformed control hypocotyl segments were returned to the Percival™ growth chamber under reduced light intensity (by covering the plates with aluminum foil), and the treated hypocotyl segments were co-cultivated with *Agrobacterium* for 3 days.

Callus Induction on Selection Medium:

After 3 days of co-cultivation, the hypocotyl segments were individually transferred with forceps onto callus induction medium, MSK1D1H1 (MS, 1 mg/L kinetin, 1 mg/L 2,4-D, 0.5 gm/L MES, 5 mg/L AgNO$_3$, 300 mg/L Timentin™, 200 mg/L carbenicillin, 1 mg/L Herbiace™, 3% sucrose, 0.7% phytagar) with growth regime set at 22-26° C. The hypocotyl segments were anchored on the medium but were not deeply embedded into the medium.

Selection and Shoot Regeneration:

After 7 days on callus induction medium, the callusing hypocotyl segments were transferred to Shoot Regeneration Medium 1 with selection, MSB3Z1H1 (MS, 3 mg/L BAP, 1 mg/L zeatin, 0.5 gm/L MES, 5 mg/L AgNO$_3$, 300 mg/L Timentin™, 200 mg/L carbenicillin, 1 mg/L Herbiace™, 3% sucrose, 0.7% phytagar). After 14 days, the hypocotyl segments which had developed shoots were transferred to Regeneration Medium 2 with increased selection, MSB3Z1H3 (MS, 3 mg/L BAP, 1 mg/L Zeatin, 0.5 gm/L MES, 5 mg/L AgNO$_3$, 300 mg/l Timentin™, 200 mg/L carbenicillin, 3 mg/L Herbiace™, 3% sucrose, 0.7% phytagar) with growth regime set at 22-26° C.

Shoot Elongation:

After 14 days, the hypocotyl segments that had developed shoots were transferred from Regeneration Medium 2 to shoot elongation medium, MSMESH5 (MS, 300 mg/L Timentin™, 5 mg/l Herbiace™, 2% sucrose, 0.7% TC Agar) with growth regime set at 22-26° C. Shoots that were already elongated were isolated from the hypocotyl segments and transferred to MSMESH5. After 14 days the remaining shoots which had not elongated in the first round of culturing on shoot elongation medium were transferred to fresh shoot elongation medium, MSMESH5. At this stage all remaining hypocotyl segments which did not produce shoots were discarded.

Root Induction:

After 14 days of culturing on the shoot elongation medium, the isolated shoots were transferred to MSMEST medium (MS, 0.5 g/L MES, 300 mg/L Timentin™, 2% sucrose, 0.7% TC Agar) for root induction at 22-26° C. Any shoots which did not produce roots after incubation in the first transfer to MSMEST medium were transferred for a second or third round of incubation on MSMEST medium until the shoots developed roots.

PCR Analysis:

Transformed canola hypocotyl segments which regenerated into shoots comprising roots were further analyzed via a PCR molecular confirmation assay. Leaf tissue was obtained from the green shoots and tested via the PCR for the presence of the pat selectable marker gene. Any chlorotic shoots were discarded and not subjected to the PCR analysis. Samples that were identified as positive for presence of the pat selectable marker gene were kept and cultured on the MSMEST medium to continue development and elongation of the shoots and roots. The samples that were identified as not containing the pat selectable marker gene negative according to the PCR analysis were discarded.

The transformed canola plants comprising shoots and roots that were PCR-positive for the presence of the pat selectable marker gene were transplanted into soil in a greenhouse. After establishment of the canola plants within soil, the canola plants were further analyzed to quantitate the copy number of the pat gene expression cassette via an Invader™ quantitative PCR assay and Southern blotting. Transgenic $T_0$ canola plants which were confirmed to contain at least one copy of the pat gene expression cassette were advanced for further analysis of the seed fatty acid profile. The seeds obtained from theses transgenic $T_0$ canola plants, i.e., $T_1$ canola seeds, were analyzed via a FAME analysis method to identify events which comprise a reduction in total saturated fatty acids (total saturated fatty acid content was determined by summing all of the saturated fatty acids, including short and long chain fatty acids) as compared to control plants.

Example 3

FAME Analysis of $T_1$ Canola Seeds Obtained from Transgenic pDAB7305 Canola Plants Segregating $T_1$ canola seeds were analyzed via a FAME analysis method to identify $T_0$ canola events which produced $T_1$ canola seeds comprising a reduction in total saturated fatty acids (C14:0, C16:0, C18:0, C20:0, C22:0, C24:0) as compared to seeds obtained from control plants grown in the same conditions. The sum of all Total Saturated Fatty Acids (TSFA) were quantitated and compared to a negative control plant. The FAME analysis was completed using the protocol described below on a single $T_1$ canola seed. A total of 24 single $T_1$ canola seed from each individual canola $T_0$ event were assayed and the TSFA results from each single were quantitated.

Single canola seed samples were homogenized in heptane containing triheptadecanoin (Nu-Chek prep) as a triacylglycerol internal standard, using steel ball mill. Prior to homogenization, a solution of 0.25 M of freshly prepared sodium methoxide (Sigma-Aldrich, St. Louis, Mo.) in methanol was added. Extraction was conducted at 40° C. with constant shaking. Endogenous fatty acid recoveries were normalized by the recovery of the methylated surrogate C17 fatty acid. Extraction of FAMEs (fatty acid methyl esters) was repeated three times and the heptane layers were pooled prior to analysis. The resulting FAMEs were analyzed by GC-FID using a capillary column BPX 70 from SGE (15 m×0.25 mm×0.25 μm). Each FAME was identified by retention time and quantified by the injection of a rapeseed oil reference mix from Matreya LLC (Pleasant Gap, Pa.) as a calibration standard with addition of appropriate long chain fatty acids (Nu-Chek Prep, Elysian Minn.).

The bulk seed analysis consisted of 50 mg aliquot (10 to 15 seeds combined) and followed the same protocol described above with a slight modification. In order to drive the reaction of derivatization to completeness, the oil was first extracted three times with heptane. Then an aliquot of the combined oil extract, corresponding to 1 seed, was derivatized in FAMEs as described in the single seed protocol above. The completeness of the reaction was verified by checking for the presence of endogenous FAMEs in a fourth extraction/derivatization.

Three transgenic canola events (Event 2182[12]-138.001, Event 2182[12]-125.001, and Event 2182[12]-156.001) were identified and selected for advancement to the $T_1$ generation based on the FAME results which indicated a significant reduction in TSFA as compared to control canola plants. Two additional categories of plant fatty acid content were assayed. These categories included the Mono Unsaturated Fatty Acid (MUFA: C16:1, C18:1 and C20:1) and Poly Unsaturated Fatty Acid (PUFA: C18:2 and C18:3) concentrations, are listed to show the effect of lowering TSFA in $T_1$ seed. (Table 1).

TABLE 1

Summary composition of single $T_1$ seed TSFA, MUFA and PUFA accumulations obtained from three transgenic canola events as compared to several NEXERA 710 ™ non-transformed control plants.

| | | TSFA (%) | | | MUFA (%) | | | PUFA (%) | | |
|---|---|---|---|---|---|---|---|---|---|---|
| Event | N* | Mean | Min | Max | Mean | Min | Max | Mean | Min | Max |
| 2182[12]-125.001 | 23 | 3.16 | 2.30 | 4.30 | 82.74 | 74.00 | 90.20 | 14.09 | 6.50 | 22.20 |
| 2182[12]-138.001 | 24 | 3.40 | 2.70 | 4.70 | 84.10 | 80.40 | 88.90 | 12.50 | 8.00 | 16.30 |
| 2182[12]-156.001 | 23 | 3.49 | 2.80 | 5.00 | 87.30 | 83.00 | 90.70 | 9.23 | 6.00 | 12.50 |
| NEXERA 710.1.16 | 24 | 6.96 | 6.10 | 8.00 | 80.23 | 76.90 | 82.40 | 12.82 | 10.50 | 16.20 |
| NEXERA 710.1.22 | 24 | 6.94 | 5.90 | 8.40 | 79.91 | 77.40 | 82.60 | 13.15 | 10.60 | 16.40 |
| NEXERA 710.1.29 | 24 | 7.06 | 6.10 | 8.50 | 77.33 | 73.20 | 81.70 | 15.64 | 11.50 | 19.40 |
| NEXERA 710.1.5__ | 24 | 6.99 | 6.20 | 7.80 | 82.71 | 78.50 | 84.40 | 10.28 | 8.20 | 13.90 |

N* indicates the number of individual $T_1$ seed analyzed for each plant progeny.

The mean TSFA of the transgenic canola events is reduced significantly as compared to the NEXERA 710™ non-transformed control plants. Concomitant to the reduction of TSFA an increase in MUFA content (C18:1 and C16:1) was observed. The increase in MUFA content is the direct result from the over-expression of the AnD9DS introducing a double bond at the $9^{th}$ carbon (Δ9) from the carboxylic function of saturated fatty acid. Interestingly, the PUFA content did not increase with the accumulation of MUFA substrate of phosphoglycerolipid desaturase FAD2 synthesizing C18:2.

Figure 3:
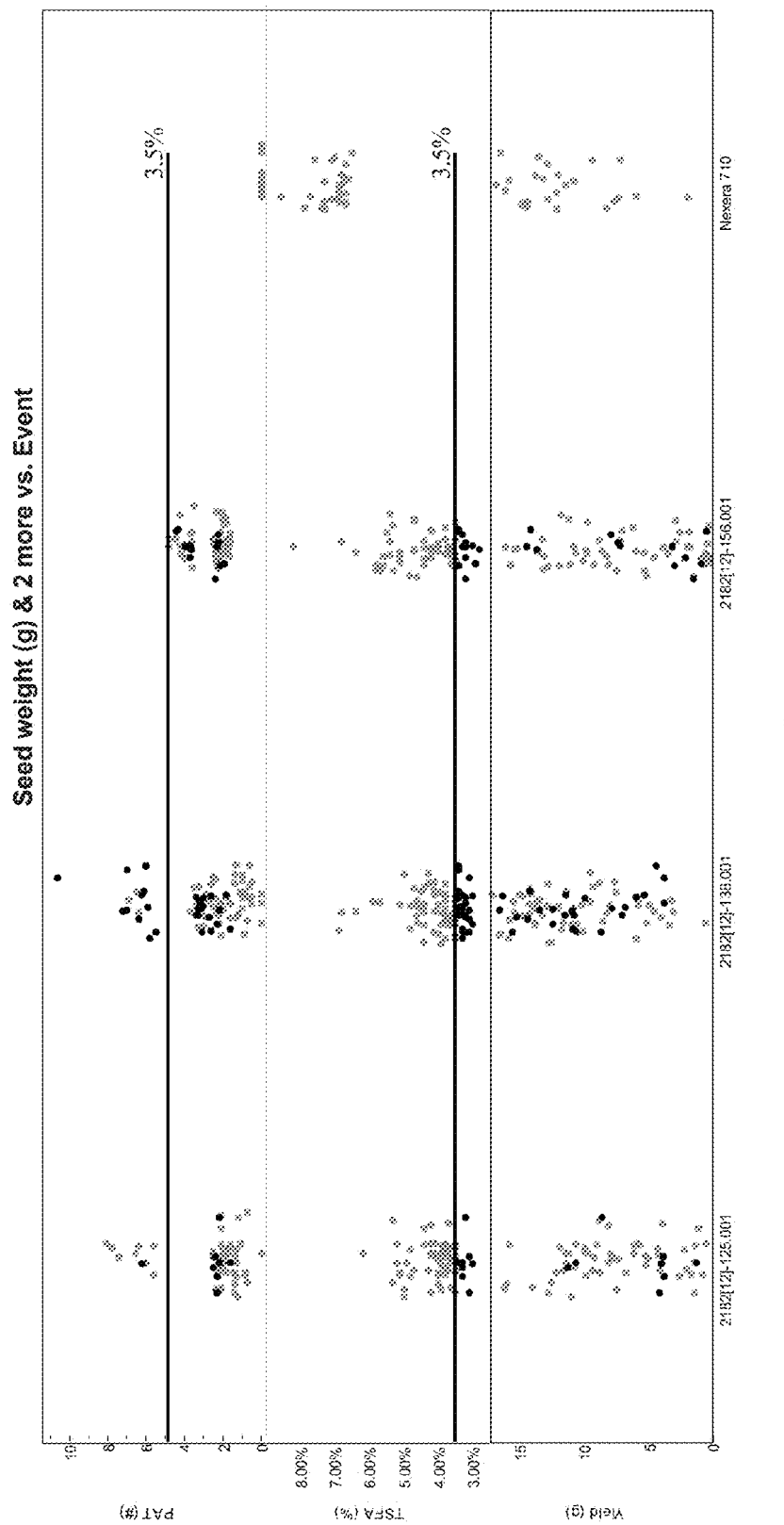
FIG. 3 shows the distribution of TSFA in $T_2$ seed population from three selected transgenic events as compared to the negative control NEXERA 710™ canola plants. Dark dots represent seed progeny with a TSFA lower than 3.5% (dark line). As indicated in the graph, the plants with a TSFA lower than 3.5% produced varying amounts of yield and possessed from 2 to 10 copies numbers of the pat transgene that is contained on the same T-strand integrant as the AnD9DS transgene.

$T_1$ canola plant events were grown in a greenhouse and self-fertilized to fix the introgressed transgene in progeny plants. Invader™ quantitative PCR assays were completed on multiple $T_1$ canola plants from each transgenic event. These results indicated that the $T_1$ canola plants obtained from each of the three events contained about 2 or 3 copies of the pDAB7305 T-strand integration (FIG. 3 top panel). A specific determination of copy number was unobtainable, as the pDAB7305 T-strand integrant segregated at varying copy numbers across the three events. The $T_1$ canola plant events were grown in the greenhouse to maturity and self-fertilized. The resulting $T_2$ canola seed was harvested for fatty acid profile analysis via FAME assay.

Example 4

Figure 2:
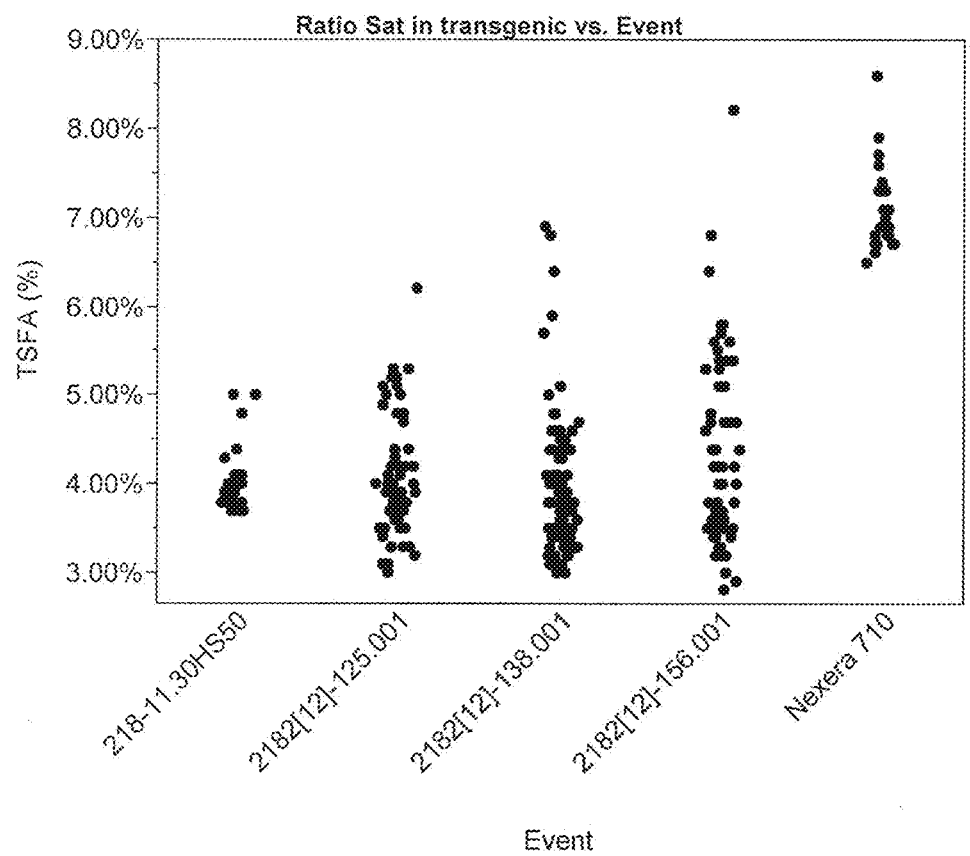
FIG. 2 illustrates the distribution of TSFA (%) in bulk $T_2$ seed from segregating $T_1$ canola plants compared to NEXERA 710™ canola control plants and the positive control plants comprised of the 218-11.30HL transgenic canola plants.

FAME Analysis of $T_2$ Canola Seeds Obtained from Transgenic pDAB7305 Canola Plants Bulked $T_2$ canola seeds were analyzed via the previously described FAME analysis method to identify $T_1$ canola plant lines which comprised a reduction in total saturated fatty acids as compared to control plants (NEXERA 710™). (FIG. 2). The yield of each plant was recorded as gram of seed per plant. The yield results were compared to the yield of a transgenic positive control event, 218-11.30 (also described herein as 218-11.30HS50 or 218-11.30HL) containing a stably integrated *Aspergillus nidulans* delta-9 desaturase transgene (See, WO 2006/042049) that was grown alongside the transgenic plants of the subject disclosure. Both the 218-11.30 plants and the transgenic canola plants of the subject disclosure express a similar transgene. However, the construct used in the transformation of the 2182[12]-125.Sx001, 2182[12]-138.Sx001 and 2182[12]-156.Sx00 canola plants in the subject disclosure is different, as it contains a second PTU comprised of a *Lesquerella fendleri* KCS3 promoter driving expression of a AnD9DS coding sequence, and flanked by the *Agrobacterium tumefaciens* ORF 23 3' untranslated region.

The TSFA (%) of the transgenic plants of the subject disclosure were quantitated and compared to the TSFA (%) obtained from the positive control, 218-11.30HL transgenic canola plants and the negative control, NEXERA 710™ plants. A small number of transgenic plants of the subject disclosure were identified to contain higher levels of TSFA, at levels similar to the negative control NEXERA 710™ plants. These plants are sibling nulls which resulted from segregation of the transgenes during self-fertilization, and do not contain any actively expressing copies of the transgenes of the subject disclosure. These results confirmed that the total saturated fatty acid content of the bulked $T_2$ canola seed was reduced below 3.5% in identified $T_1$ canola plant.

The $T_2$ canola lines were further analyzed to determine which canola lines contained low copy numbers of the pDAB7305 T-strand integrant and produced the high $T_2$ seed yield. (FIG. 3).

Individual canola plants of the subject disclosure were selected which contained less than 3.5% TSFA, produced more than 10 g of yield, and contained the lowest T-strand copy number. Based on these three criteria (levels of TSFA below 3.5%, high seed yield, and low copy number) seven canola plants were selected and advanced for further characterization of the TSFA profile. Copy number was determined from one plant per T1 line, using an Invader Assay. Table 2. These $T_2$ canola plant lines were transferred to the greenhouse, grown to maturity and self-fertilized. The $T_2$ canola plant lines were further analyzed molecularly and the $T_3$ seed was harvested for fatty acid profile analysis via FAME assay.

Example 5

Molecular Confirmation of $T_2$ Canola Lines

Selected $T_2$ canola events which contained the pat gene expression cassette (and the closely linked AnD9DS gene expression cassettes) were characterized for their molecular integration pattern using quantitative PCR and Southern blot analysis.

AnD9DS Integration Confirmation via Hydrolysis Probe Assay

The presence of the AnD9DS gene expression cassette was confirmed via hydrolysis probe assays. Isolated $T_2$ canola plants were initially screened via a hydrolysis probe assay, analogous to TAQMAN™, to confirm the presence of the pat transgenes. The data generated from these studies was used to determine the transgene copy number and used to select transgenic canola events for back crossing and advancement to subsequent generations.

Tissue samples were collected in 96-well plates, tissue maceration was performed with a KLECO™ tissue pulverizer and stainless steel beads (Hoover Precision Products, Cumming, Ga.), in Qiagen RLT™ buffer. Following tissue maceration, the genomic DNA was isolated in high-throughput format using the Biosprint 96™ Plant kit (Qiagen, Germantown, Md.) according to the manufacturer's suggested protocol. Genomic DNA was quantified by Quant-IT Pico Green DNA assay Kit™ (Molecular Probes, Invitrogen, Carlsbad, Calif.). Quantified genomic DNA was adjusted to around 2 ng/µL for the hydrolysis probe assay using a BIOROBOT3000™ automated liquid handler (Qiagen, Germantown, Md.). Transgene copy number determination by hydrolysis probe assay, analogous to TAQMAN® assay, was performed by real-time PCR using the LIGHTCYCLER® 480 system (Roche Applied Science, Indianapolis, Ind.). Assays were designed for pat and an internal reference gene HMG1 (Weng et al. (2005). J. AOAC Int. 88(2):577-84) using the LIGHTCYCLER® Probe Design Software 2.0. For amplification, LIGHTCYCLER® 480 Probes Master mix (Roche Applied Science, Indianapolis, Ind.) was prepared at 1× final concentration in a 10 µL volume multiplex reaction containing 0.4 µM of each primer for AnD9DS and pat and 0.2 µM of each probe (Table 3). A two-step amplification reaction was performed with an extension at 60° C. for 40 seconds with fluorescence acquisition. All samples were run and the averaged Cycle threshold (Ct) values were

TABLE 2

The $T_2$ canola lines which were selected based on highest yield (seed weight), lowest PAT copy number (T1 plants) and lowest TSFA are listed.

| Event | Plant Line | Seed Weight (g) | PAT (Copy Number) | TSFA (%) |
|---|---|---|---|---|
| 2182[12]-138.001 | 2182[12]-138.Sx001.sSx085 | 16.37 | 2.6 | 3.03 |
| | 2182[12]-138.Sx001.Sx090 | 16.58 | 2.2 | 3.11 |
| | 2182[12]-138.Sx001.Sx094 | 12.47 | 2.3 | 3.02 |
| | 2182[12]-138.Sx001.Sx029 | 18 | 3.0 | 3.31 |
| | 2182[12]-138.Sx001.Sx084 | 15.59 | 3.1 | 3.08 |
| 2182[12]-125.001 | 2182[12]-125.Sx001.Sx014 | 11.26 | 2.5 | 3.27 |
| 2182[12]-156.001 | 2182[12]-156.Sx001.Sx049 | 14.44 | 2.3 | 3.28 | used for analysis of each sample. Analysis of real time PCR data was performed using LIGHTCYCLER® software release 1.5 using the relative quant module and is based on the ΔΔCt method. Controls included a sample of genomic DNA from a single copy calibrator and known two copy check that were included in each run. Table 4 lists the results of the hydrolysis probe assays. Copy number was determined from N plants per T1 line (and averaged, giving the value in Table 4), using an qPCR Assay.

TABLE 3

Primer and probe sequences used for hydrolysis probe assay of pat and internal reference (HMG1).

| Gene Detected | Forward Primer | Reverse Primer | Probe | Label |
|---|---|---|---|---|
| PAT v5 | SEQ ID NO: 6 acaagagtgga ttgatgatcta gagaggt | SEQ ID NO: 7 ctttgatgccta tgtgacacgtaa acagt | SEQ ID NO: 8 ccagcgtaagca ataccagccaca acacc | FAM |
| HMG1 | SEQ ID NO: 9 cctctctacca ccgtctcacat g | SEQ ID NO: 10 gatctggccgga ctgtttcaca | SEQ ID NO: 11 cgctcctcagct accacctcaac | HEX |

TABLE 4

Copy amount results for the AnD9DS events (T2 plants) as determined using the hydrolysis probe assay.

| | | PAT gene | | |
|---|---|---|---|---|
| Event/Line | N | mean | SD | CV (%) |
| 218-11.30(HL) | 12 | 3.61 | 0.28 | 7.82 |
| 2182[12]-125.Sx001.Sx014 | 35 | 5.93 | 0.98 | 16.48 |
| 2182[12]-138.Sx001.Sx085 | 34 | 9.40 | 1.03 | 11.00 |
| 2182[12]-138.Sx001.Sx090 | 33 | 7.69 | 0.35 | 4.54 |
| 2182[12]-138.Sx001.Sx094 | 35 | 9.98 | 0.79 | 7.93 |
| 2182[12]-156.Sx001.Sx049 | 33 | 4.35 | 0.48 | 11.12 |

The results of the hydrolysis probe assay identified two lines (2182[12]-138.Sx001.Sx094 and 2182[12]-138.SX001.Sx090) which had a combination of relative standard deviation (shown in Table 4 as SD) and coefficient of variation (shown in Table 4 as CV %) that were comparable to the positive control plants (218-11.30(HL)). The 218-11.30(HL) control plants were previously identified to contain two fixed copies of the AnD9DS gene insertion (WO 2006042049). By comparing the selected canola lines (2182 [12]-138.Sx001.Sx094 and 2182[12]-138.SX001.Sx090) to the 218-11.30(HL) control plants, specific canola lines were identified which would contain fixed copies of the pDAB7305 T-strand integrants.

AnD9DS Genomic Integration Confirmation via Southern Blot Analysis.

Southern blot analysis was used to establish the integration pattern of the inserted T-strand DNA fragment and identify canola lines which contained a full length AnD9DS gene expression cassette. Data were generated to demonstrate the integration and integrity of the transgene inserts within the canola genome. The detailed Southern blot analysis was conducted using a PCR amplified probe specific to the AnD9DS gene expression cassette. The hybridization of the probe with genomic DNA that had been digested with specific restriction enzymes identified genomic DNA fragments of specific molecular weights, the patterns of which were used to characterize the transgenic events for advancement to the next generation.

Tissue samples were collected in 2 mL conical tubes and lyophilized for 2 days. Tissue maceration was performed with a KLECKO™ tissue pulverizer and tungsten beads. Following tissue maceration, the genomic DNA was isolated using a CTAB isolation procedure. The genomic DNA was further purified using the Qiagen Genomic Tips™ kit. Genomic DNA was quantified by Quant-IT Pico Green DNA™ assay kit (Molecular Probes, Invitrogen, Carlsbad, Calif.). Quantified genomic DNA was adjusted to a consistent concentration.

For each sample, 4 μg of genomic DNA was thoroughly digested with the restriction enzyme BamHI (New England Biolabs, Beverley, Mass.). The digested DNA was concentrated by precipitation with Quick Precipitation Solution™ (Edge Biosystems, Gaithersburg, Md.) according to the manufacturer's suggested protocol. The genomic DNA was then resuspended in 25 μL of water at 65° C. for 1 hour. Resuspended samples were loaded onto a 0.8% agarose gel prepared in 1×TAE and electrophoresed overnight at 1.1 V/cm in 1×TAE buffer. The gel was sequentially subjected to denaturation (0.2 M NaOH/0.6 M NaCl) for 30 minutes, and neutralization (0.5 M Tris-HCl (pH 7.5)/1.5 M NaCl) for 30 minutes.

Transfer of DNA fragments to nylon membranes was performed by passively wicking 20×SSC solution overnight through the gel onto treated IMMOBILON™ NY+ transfer membrane (Millipore, Billerica, Mass.) by using a chromatography paper wick and paper towels. Following transfer, the membrane was briefly washed with 2×SSC, cross-linked with the STRATALINKER™ 1800 (Stratagene, LaJolla, Calif.), and vacuum baked at 80° C. for 3 hours.

Blots were incubated with pre-hybridization solution (Perfect Hyb plus, Sigma, St. Louis, Mo.) for 1 hour at 65° C. in glass roller bottles using a model 400 hybridization incubator (Robbins Scientific, Sunnyvale, Calif.). Probes were prepared from a PCR fragment containing the entire coding sequence. The PCR amplicon was purified using QIAEX II gel extraction Kit™ and labeled with DIG DNA Labeling Kit™ (Roche Applied BioSciencse, Indianapolis, Ind.). Blots were hybridized overnight at 65° C. with denatured probe added directly to hybridization buffer. Following hybridization, blots were sequentially washed at 65° C. with 0.1×SSC/0.1% SDS for 40 minutes. Finally, the blots were exposed to storage phosphor imaging screens and imaged using a Molecular Dynamics Storm 860™ imaging system.

The Southern blot analyses completed in this study were used to determine the copy number and confirm that selected events contained the AnD9DS gene expression cassette within the genome of canola. Table 5 provides the banding profile of multiple $T_2$ plants from selected lines based on the criteria defined above in Table 2. The control lines did not contain the selectable marker confirming the PCR data. Most of the lines selected from the three events show a homogeneous band pattern (number and size) except line from event 2182[12]-125.Sx001.Sx014. All three T2 lines from event 2182[12]-138.Sx001 display T2 populations with consistent banding pattern.

TABLE 5

Summary of Southern analysis completed on multiple $T_2$ canola lines from four transgenic events and the NEXERA 710 ™ canola control plants. The sizes of the observed bands for each sample were sized by comparison to a known standard run beside the samples on an agarose gel.

| Event- $T_2$ Line | Number of Plants | Band Numbers | Size Observed (Kb) |
|---|---|---|---|
| NEXERA 710 ™ | 2 | 0 | NA |
| 218-11.30(HL) | 2 | 4 | 5.8, 3.5, 1, 0.35* |
| 2182[12]-125.Sx001.Sx014 | 8 | 3 bands (2 plants) and 4 bands (6 plants) | 9.2, 4.4, 3.5, 2.6, 0.5 |
| 2182[12]-138.Sx001.Sx085 | 8 | 4 | 9.2, 5.8, 3.5, 0.7 |
| 2182[12]-138.Sx001.Sx090 | 8 | 4 | 9.2, 5.1, 2.5, 0.6 |
| 2182[12]-138.Sx001.Sx094 | 8 | 4 | 9.2, 5.1, 2.5, 0.6 |
| 2182[12]-156.Sx001.Sx049 | 8 | 2 | 4.5, 3.9 |

Example 6

$T_3$ Seed Yield of Selected Canola Lines

Selected plants from the $T_2$ canola lines were grown to maturity in the greenhouse. Seed was harvested from the plants. The seed was cleaned and the yield of seed per $T_2$ canola line was determined (Table 6). The yield of the seed from each line and compared to the yield of seed obtained from the untransformed control plants (Nexera™ 710GS) grown in the same conditions. Table 6 presents the yield results for the various plants which were obtained from each $T_2$ canola line. These results illustrate that the yield was variable for each plant and line tested. But that the average amounts of yield of the $T_2$ canola lines (2182[12]-125.Sx001.Sx014, 2182[12]-138.Sx001.Sx085, 2182[12]-138.Sx001.5x090, 2182[12]-138.Sx001.5x094, and 2182[12]-156.Sx001.Sx049) were relatively similar and did not significantly deviate from the control plants (Nexera™ 710G5 and 218-11.30(HL)).

Example 7

FAME Analysis of $T_3$ Canola Seeds Obtained from Transgenic pDAB7305 Canola Plants Both, single and bulked $T_3$ canola seeds were analyzed via the previously described FAME analysis method to characterize the fatty acid profile of the lines to identify specific lines which resulted in a reduction in total saturated fatty acids as compared to control plants. The sum of the total saturated fatty acids were quantitated and compared to positive control and negative control plants. The results confirmed that the total saturated fatty acid and saturated fatty acid (as determined from the sum of palmitic and stearic acid content) content of the single and bulked $T_3$ canola seed was reduced below 3.5% in the selected canola plant lines.

Surprisingly, two lines, 2182[12]-138.Sx001.Sx085 and 2182[12]-138.Sx001.Sx094, accumulated TSFA levels that averaged under 3.0%. Described for the first time are canola lines which are comprised of bulked seed that contains less than 3.0% saturated fatty acid. Table 7 and Table 8.

Figure 4:
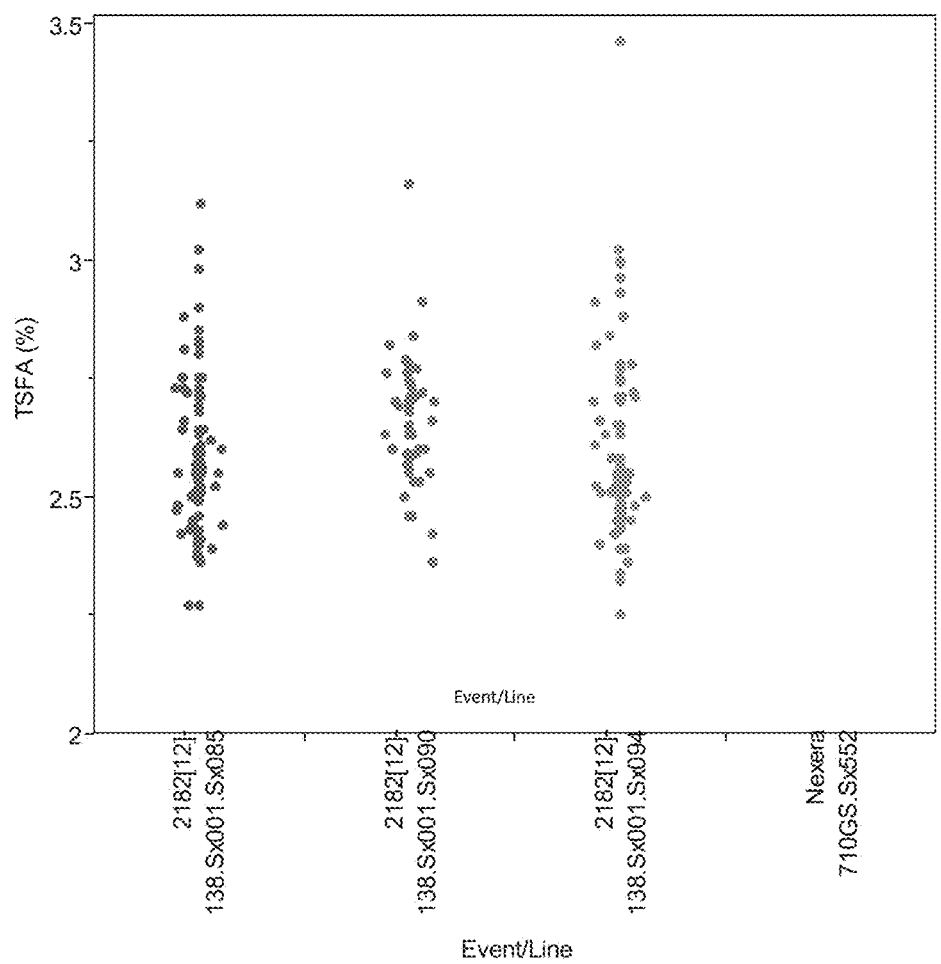
FIG. 4 illustrates the distribution of TSFA and saturated fatty acid percentage in canola single seed (wild type control plants are excluded so that the graphs depict the TSFA values of transgenic canola events).
Figure 4:
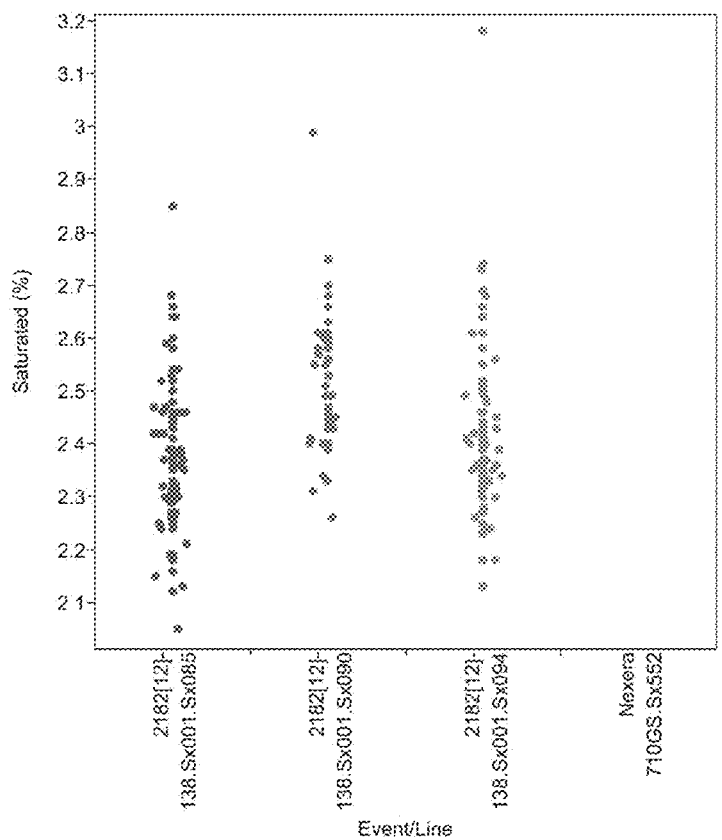

In addition, a sub-set of canola lines were used for seed FAME analysis to determine the lowest level of total saturated fatty acid and saturated fatty acid levels which could be obtained in a single canola seed. The single seed FAME analysis was completed on seeds obtained from the canola lines that were selected based on the lowest total saturated fatty acid of bulked seed and the high levels of plant yield. A total of 288 individual seeds were analyzed per line using the FAME method. The summary of the analysis is presented in Table 9. All single seeds from selected plants have a mean TSFA below 2.8%, which is significantly below the 3.5% TSFA level. The lowest TSFA level is 2.25% at the single seed canola level. This is significantly lower than the TSFA level of 5.11% which was obtained in the Nexera™ 710G5 control plants. Finally, the maximum TSFA percentage in the transgenic canola lines does not excede 3.5% and the mean saturated level in single seed is 2.52% which is well below 3.5%. Table 9 and FIG. 4.

Table 7 shows the distribution of $T_2$ mature seed bulk FAMEs analysis for five populations of genetically homogenous canola lines as compared to the untransformed Nexera™ 710G5 controls and transformed 218-11.30(HL) positive control plants. The average of all the individual measurement (N) were determined to represent TSFA and saturated percentage for the population of canola plants. Canola lines, 2182[12]-138.Sx001.Sx085 and 2182[12]-138.Sx001.Sx094 are identified via bold print as these lines had an average TSFA percentage below 3.00 percent.

TABLE 6

ANNOVA analysis of the seed yield, measured as total grams, from canola transgenic lines and the untransformed Nexera™ 710GS control plants. Yield results are not significantly different ($p < 0.05$) for plants that are connected by the same letter in parenthesis.

| Event/Line | Plant Count | Ratio | Yield (g) |
|---|---|---|---|
| 218-11.30(HL) | 12 | 0.06186 | 5.7233333 (A, B) |
| 2182[12]-125.Sx001.Sx014 | 35 | 0.18041 | 5.9874286 (A, B) |
| 2182[12]-138.Sx001.Sx085 | 34 | 0.17526 | 6.8394118 (A) |
| 2182[12]-138.Sx001.Sx090 | 33 | 0.17010 | 6.4887879 (A, B) |
| 2182[12]-138.Sx001.Sx094 | 35 | 0.18041 | 5.0302857 (B) |
| 2182[12]-156.Sx001.Sx049 | 33 | 0.17010 | 6.3715152 (A, B) |
| Nexera™ 710G5 | 12 | 0.06186 | 7.1666667 (A, B) |
| Total | 194 | 1.00000 | — |

TABLE 7

| T₂ parent line | N | TSFA (%) | | | Saturated (%) | | |
|---|---|---|---|---|---|---|---|
| — | — | Mean | Min | Max | Mean | Min | Max |
| 218-11.30(HL) | 12 | 3.94 | 3.75 | 4.21 | 3.39 | 3.19 | 3.65 |
| 2182[12]-125.Sx001.Sx014 | 35 | 3.43 | 2.59 | 4.24 | 3.08 | 2.34 | 3.74 |
| 2182[12]-138.Sx001.Sx085 | 34 | 2.92 | 2.53 | 3.65 | 2.68 | 2.31 | 3.36 |
| 2182[12]-138.Sx001.Sx090 | 33 | 3.24 | 2.66 | 3.87 | 2.93 | 2.37 | 3.59 |
| 2182[12]-138.Sx001.Sx094 | 35 | 2.98 | 2.50 | 3.52 | 2.68 | 2.24 | 3.21 |
| 2182[12]-156.Sx001.Sx049 | 33 | 3.47 | 2.50 | 4.21 | 3.15 | 2.26 | 3.73 |
| Nexera 710G5 | 12 | 6.43 | 6.14 | 6.69 | 5.19 | 4.89 | 5.40 |

Table 8 shows the lowest $T_3$ mature seed bulk FAMEs and plant yield of single $T_2$ progeny plants obtained from event 2182[12]-138.Sx0001 as compared to Nexera™ 710G5 control. The results displayed are for percentage of oil, percentage of TSFA, percentage of saturated fatty acids (as determined by summing the palmitic and stearic acid content), and seed yield.

TABLE 8

| Event/Line (T₂) | Oil (%) | TSFA (%) | Saturated (%) | TSFA Reduction (%) | Yield (g) |
|---|---|---|---|---|---|
| 2182[12]-138.Sx001.Sx094.Sx112 | 34.5 | 2.5 | 2.24 | 61.12 | 4.16 |
| 2182[12]-138.Sx001.Sx085.Sx070 | 38.7 | 2.53 | 2.31 | 60.65 | 6.05 |
| 2182[12]-138.Sx001.Sx085.Sx076 | 37.8 | 2.57 | 2.33 | 60.03 | 7.72 |
| 2182[12]-138.Sx001.Sx094.Sx122 | 39.3 | 2.65 | 2.41 | 58.79 | 5.73 |
| 2182[12]-138.Sx001.Sx090.Sx062 | 37.4 | 2.66 | 2.37 | 58.63 | 4.44 |
| Nexera 710GS.Sx552 | 43.7 | 6.28 | 5.15 | 2.33 | 6.97 |

Table 9 shows the distribution of $T_3$ single seed FAMEs analysis results from selected $T_2$ lines. The table shows the average (Mean), minimum (Min), and maximum (Max) TSFA and saturated fatty acid percentage, as compared to a Nexera™ 710G5 control canola plants that grown in the same condition. There was a reduction of total saturated fatty acids (TSFA) and saturated fatty acid level in $T_3$ seed of selected events as compared to a Nexera™ 710G5 control canola plants.

TABLE 9

| Events/Line | N | TSFA (%) | | | Saturated (%) | | |
|---|---|---|---|---|---|---|---|
| — | — | Mean | Min | Max | Mean | Min | Max |
| 2182[12]-138.Sx001.Sx085.Sx070 | 43 | 2.60 | 2.27 | 3.02 | 2.33 | 2.05 | 2.64 |
| 2182[12]-138.Sx001.Sx085.Sx076 | 48 | 2.57 | 2.27 | 3.12 | 2.40 | 2.16 | 2.85 |
| 2182[12]-138.Sx001.Sx090.Sx062 | 48 | 2.66 | 2.36 | 3.16 | 2.52 | 2.26 | 2.99 |
| 2182[12]-138.Sx001.Sx094.Sx112 | 48 | 2.51 | 2.25 | 2.78 | 2.38 | 2.13 | 2.61 |
| 2182[12]-138.Sx001.Sx094.Sx122 | 37 | 2.73 | 2.44 | 3.46 | 2.46 | 2.13 | 3.18 |
| Nexera 710GS.Sx552 | 48 | 6.34 | 5.71 | 7.52 | 5.11 | 4.73 | 5.90 |

What is claimed is:

1. A method for decreasing the amount of saturated fatty acids in a plant cell, the method comprising:
   transforming a plant cell with a nucleic acid molecule comprising a heterologous gene regulatory element operably linked to a polynucleotide encoding a delta-9 desaturase enzyme comprising an amino acid sequence that is at least 80% identical to SEQ ID NO:1,
   wherein the plant cell also comprises an extraplastidial desaturase selected from the group consisting of LnD9DS desaturase, HzD9DS desaturase, and MgD9DS desaturase,
   such that the amount of saturated fatty acids in the plant cell is decreased.

2. A plant seed which expresses an extraplastidial desaturase selected from the group consisting of LnD9DS desaturase, HzD9DS desaturase, and MgD9DS desaturase, and comprises a nucleic acid molecule comprising a polynucleotide encoding a delta-9 desaturase enzyme comprising an amino acid sequence that is at least 80% identical to SEQ ID NO:1.

3. The plant seed of claim 2, wherein the extraplastidial desaturase comprises an amino acid sequence selected from the group consisting of SEQ ID NOs:26-28.

4. An oil seed plant comprising a polynucleotide encoding a delta-9 desaturase enzyme comprising an amino acid sequence that is at least 80% identical to SEP ID NO:1, and further comprising an extraplastidial desaturase selected from the group consisting of LnD9DS desaturase, HzD9DS desaturase, and MgD9DS desaturase.

5. A plant material comprising a polynucleotide encoding a delta-9 desaturase enzyme comprising an amino acid sequence that is at least 80% identical to SEP ID NO:1, and further comprising an extraplastidial desaturase selected from the group consisting of LnD9DS desaturase, HzD9DS desaturase, and MgD9DS desaturase.

6. The plant material of claim 5, wherein the extraplastidial desaturase comprises an amino acid sequence selected from the group consisting of SEQ ID NOs:26-28.

* * * * *